US009365855B2

(12) United States Patent
Vaught et al.

(10) Patent No.: US 9,365,855 B2
(45) Date of Patent: Jun. 14, 2016

(54) APTAMERS TO 4-1BB AND THEIR USE IN TREATING DISEASES AND DISORDERS

(71) Applicant: SomaLogic, Inc., Boulder, CO (US)

(72) Inventors: Jonathan Vaught, Boulder, CO (US); Daniel I. Resnicow, Boulder, CO (US); Sheela Waugh, Erie, CO (US); Sheri K. Wilcox, Longmont, CO (US); Daniel J. Schneider, Arvada, CO (US)

(73) Assignee: SOMALOGIC, INC., Boulder, CO (US)

( * ) Notice: Subject to any disclaimer, the term of this patent is extended or adjusted under 35 U.S.C. 154(b) by 0 days.

(21) Appl. No.: 14/084,411

(22) Filed: Nov. 19, 2013

(65) Prior Publication Data

US 2014/0081011 A1     Mar. 20, 2014

Related U.S. Application Data

(62) Division of application No. 13/582,332, filed as application No. PCT/US2011/027064 on Mar. 3, 2011, now abandoned.

(51) Int. Cl.

| C07H 21/04 | (2006.01) |
|---|---|
| C12N 15/11 | (2006.01) |
| A61K 48/00 | (2006.01) |
| C12N 15/115 | (2010.01) |
| A61K 31/7115 | (2006.01) |
| C07H 19/073 | (2006.01) |
| C07H 19/10 | (2006.01) |

(52) U.S. Cl.
CPC .......... *C12N 15/115* (2013.01); *A61K 31/7115* (2013.01); *C07H 19/073* (2013.01); *C07H 19/10* (2013.01); *C07H 21/04* (2013.01)

(58) Field of Classification Search
None
See application file for complete search history.

(56) References Cited

U.S. PATENT DOCUMENTS

| 4,711,955 A | 12/1987 | Ward |
| 4,737,453 A | 4/1988 | Primus et al. |
| 4,752,566 A | 6/1988 | Collins et al. |
| 4,948,882 A | 8/1990 | Ruth |
| 5,270,163 A | 12/1993 | Gold et al. |
| 5,412,087 A | 5/1995 | McGall et al. |
| 5,428,149 A | 6/1995 | Eaton |
| 5,475,096 A | 12/1995 | Gold et al. |
| 5,496,938 A | 3/1996 | Gold et al. |
| 5,567,588 A | 10/1996 | Gold et al. |
| 5,580,972 A | 12/1996 | Tu |
| 5,582,981 A | 12/1996 | Toole et al. |
| 5,595,877 A | 1/1997 | Gold et al. |
| 5,599,720 A | 2/1997 | Ekins et al. |
| 5,660,985 A | 8/1997 | Pieken et al. |
| 5,719,273 A | 2/1998 | Tu et al. |
| 5,840,867 A | 11/1998 | Toole et al. |
| 5,861,254 A | 1/1999 | Schneider et al. |
| 5,945,527 A | 8/1999 | Tu et al. |
| 5,958,691 A | 9/1999 | Pieken |
| 5,962,225 A | 10/1999 | Ramberg |
| 6,020,483 A | 2/2000 | Beckvermit et al. |
| 6,175,001 B1 | 1/2001 | Barbas et al. |
| 6,344,318 B1 | 2/2002 | Gold et al. |
| 6,346,611 B1 | 2/2002 | Pagratis et al. |
| 6,734,172 B2 | 5/2004 | Scholler et al. |
| 7,855,054 B2 | 12/2010 | Schneider et al. |
| 7,947,447 B2 | 5/2011 | Zichi et al. |
| 2003/0054360 A1 | 3/2003 | Gold et al. |
| 2003/0190617 A1 | 10/2003 | Raymond et al. |
| 2004/0102413 A1 | 5/2004 | McSwiggen et al. |
| 2004/0137010 A1 | 7/2004 | Wilson et al. |
| 2004/0142335 A1 | 7/2004 | Petersohn et al. |
| 2004/0176282 A1 | 9/2004 | Dalby et al. |
| 2005/0142582 A1 | 6/2005 | Doyle et al. |
| 2005/0288244 A1 | 12/2005 | Manoharan et al. |
| 2006/0105341 A1 | 5/2006 | Krause et al. |
| 2007/0003950 A1 | 1/2007 | Shen et al. |
| 2007/0161015 A1 | 7/2007 | Zheng et al. |
| 2007/0166740 A1 | 7/2007 | Heil et al. |
| 2008/0207523 A1 | 8/2008 | Friebe et al. |
| 2009/0004667 A1 | 1/2009 | Zichi et al. |
| 2009/0130650 A1 | 5/2009 | Tan et al. |
| 2010/0285479 A1 | 11/2010 | Jenison |
| 2010/0317120 A1 | 12/2010 | Heil et al. |
| 2011/0136099 A1 | 6/2011 | Schneider et al. |
| 2011/0245479 A1 | 10/2011 | Zichi et al. |
| 2015/0148237 A1 | 5/2015 | Zichi et al. |

FOREIGN PATENT DOCUMENTS

| CA | 2738129 A1 | 4/2010 |
| GB | 2 183 661 | 6/1987 |
| WO | WO 92/14842 | 3/1992 |
| WO | WO 92/14843 | 9/1992 |
| WO | WO 2008/058291 | 5/2008 |

OTHER PUBLICATIONS

Ohuchi et al., Selection of RNA aptamers against recombinant transforming growth factor-beta type III receptor displayed on cell surface, 2006, Biochimie, vol. 88, pp. 897-904.*
McNamara et al. (2008) The Journal of Clinical Investigation 118(1):376-386 "Multivalent 4-1BB binding aptamers costimulate CD8+ T cells and inhibit tumor growth in mice."
Bartel et al. (1991) Cell 67:529-536, "HIV-1 Rev Regulation Involves Recognition of Non-Watson-Crick Base Pairs in Viral RNA".
Bock et al., (1992) Nature 355:564-565 "Selection of Single-Stranded DNA Molecules That Bind and Inhibit Human Thrombin".
Daniels et al. (Dec. 23, 2003) PNAS 100(26):15416-15421, "A tenascin-C aptamer identified by tumor cell SELEX: Systematic evolution of ligands by exponential enrichment".
DiDonato (2006) "Dissertation. Part II. Synthesis and Evaluation of Modified Nucleotides for DNA Aptamer Selection" University of North Carolina, Raleigh 30-53.

(Continued)

*Primary Examiner* — Dana Shin
(74) *Attorney, Agent, or Firm* — Swanson & Bratschun, L.L.C.

(57) ABSTRACT

The present disclosure relates generally to the field of nucleic acids and, more particularly, to aptamers capable of binding to 4-1BB; pharmaceutical compositions comprising such 4-1BB aptamers; and methods of making and using the same.

15 Claims, 10 Drawing Sheets

(56) References Cited

OTHER PUBLICATIONS

Drabovich et al. (May 1, 2006) Analytical Chemistry 78(9):3171-3178, "Selection of smart aptamers by methods of kinetic capillary electrophoresis".
Eaton et al. (1997) Bioorganic & Medicinal Chemistry 5(6):1087-1096, "Post-SELEX Combinatorial Optimization of Aptamers".
Ekins and Chu (Sep. 1997) JIFCC 9(3):100-109, "Immunoassay and Other Ligand Assays: Present Status and Future Trends".
Ellington & Szostak (1990) "Selection of RNAs with ligand-specific binding activity from pools of random sequence molecules" RNA Processing meeting abstract, p. 84.
Extended European Search Report issued Sep. 19, 2013 in EP 11751374.7.
Famulok and Szostak (1992) Angew. Chem. Int. Ed. Engl. 31(8): 979-988, "In Vitro Selection of Specific Ligand-binding Nucleic Acids".
Gebhardt et al. (Jun. 20, 2000) Biochemistry 39(24):7255-7265, "RNA aptamers to S-adenosylhomocysteine: kinectic properties, divalent cation dependency, and comparision with anti-S-adenosylhomocysteine antibody".
Gold et al. (Jan. 1, 1995) Harvey Lectures 91:47-57, "The SELEX Process: A Surprising Source of Therapeutic and Diagnostic Compounds".
ISR and Written Opinion mailed Jul. 20, 2011 in PCT/US2011/027064.
Jhaveri et al. (Sep. 8, 1998) Bioorganic & Medicinal Chemistry Letters, 8(17):2285-2290, "In vitro selection of phosphorothiolated aptamers".
Joyce (1989) Gene 82:83-87, "Amplification, mutation and selection of catalytic RNA".
Joyce and Inoue (1989) Nucleic Acids Research 17(2): 711-722, "A novel technique for the rapid preparation of mutant RNAs".
Kinzler and Vogelstein (1989) Nucleic Acids Research 17(10): 3645-3653, "Whole genome PCR: application to the identification of sequences bound by gene regulatory proteins".
Kramer et al. (1974) J. Mol. Biol. 89: 719-736, "Evolution in vitro: sequence and phenotype of a mutant RNA resistant to ethidium bromide".
Langer et al. (Nov. 1981) Proc. Natl. Acad. Sci. USA,78(11):6633-6637, "Enzymatic synthesis of biotin-labeled polynucleotides: Novel nucleic acid affinity probes".
Latham et al. (1994) Nucleic Acids Research 22(14):2817-2822, "The application of a modified nucleotide in aptamer selection: novel thrombin aptamers containing 5-(1-pentynyl)-2' -deoxyuridine".
Levisohn and Spiegleman (1968) PNAS USA 60: 866-872, "The cloning of a self-replicating RNA molecule".
Levisohn and Spiegleman (1969) PNAS USA 63: 805-811, "Further extracellular Darwinian experiments with replicating RNA moleucles: diverse variants isolated under different selective conditions".
Mayer, G. et al. (Jan. 2004) Biodrugs 18(6):351-356, "Aptamers in Research and Drug Development".
Mayer, G. et al. (Mar. 2009) Angew. Chem. Int. Ed. 48(15):2672-2689, "The Chemical Biology of Aptamers".
McGown et al. (Nov. 1995) Anal. Chem. 67:663A-668A, "The Nucleic Acid Ligand. A New Tool for Molecular Recognition".
Oliphant and Struhl (1987) Methods in Enzymology 155: 568-582, "The use of random-sequence oligonucleotides for determining consensus sequences".
Oliphant and Struhl (1988) Nucleic Acids Research 16(15): 7673-7683, "Defining the consensus sequences of E. coli promoter elements by random selection".
Oliphant et al. (1986) Gene 44:177-183, "Cloning of random-sequence oligodeoxynucleotides".
Oliphant et al. (Jul. 1989) Mol. Cell. Biol. 9: 2944-2949, "Defining the sequence specificity of DNA-binding proteins by selecting binding sites from random-sequence oligonucleotides: analysis of yeast GCN4 protein".
Osborne et al. (1997) Current Opinion in Chemical Biology 1:5-9, "Aptamers as Therapeutic and Diagnostic Reagents: Problems and Prospects".
Robertson and Joyce (Mar. 1990) Nature 344: 467-468, "Selection in vitro of an RNA enzyme that specifically cleaves single-stranded DNA".
Schoetzau et al. (2003) Bioconjugate Chemistry 14:919-926, "Aminomodified Nucleobases: Functionalized Nucleoside Triphosphates Applicable for SELEX".
Syvanen et al. (1986) Nucleic Acid Research, 14(12):5037-5048, "Fast quantification of nucleic acid hybrids by affinity-based hybrid collection".
Szostak (1988) Redesigning the Molecules of Life, (S.A. Benner ed.) Springer-Verlag Berlin Heidelberg, pp. 87-113.
Tarasow (1998) Nucleic Acid Sciences 48(1):29-37, Dressed for Success "Realizing the Catalytic Potential of RNA".
Thiesen and Bach (Jun. 1990) Nucleic Acids Res. 18(11): 3203-3209, "Target detection assay (TDA): a versatile procedure to determine DNA binding sites as demonstrated on SP1 protein".
Tuerk and Gold (Aug. 1990) Science 249: 505-510, "Systematic evolution of ligands by exponential enrichment: RNA ligands to bacteriophage T4 DNA polymerase".
Vaught et al. (Mar. 2010) J.Am. Chem. Soc. ePub, 132(12):4141-4151:4142, "Expanding the Chemistry of DNA for In Vitro Selection".
Vaught, Jonathan David, Thesis Oct. 2008, "Enhancing the Functionality of Nucleic Acids".
Zichi et al. (Mar. 7, 2008) Current Opinion in Chemical Biology 12(1):78-85, "Proteomics and diagnostics: Let's Get Specific, again".

\* cited by examiner

FIG. 1A        FIG. 1B
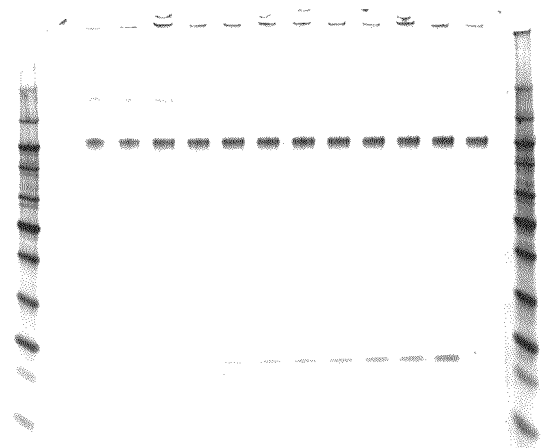
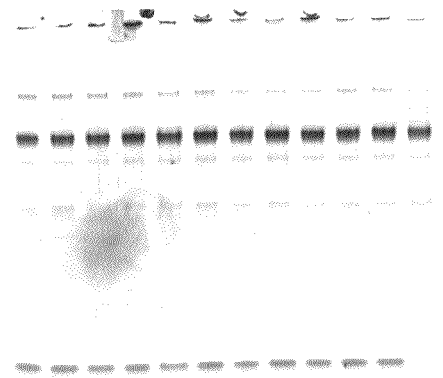
FIG. 2
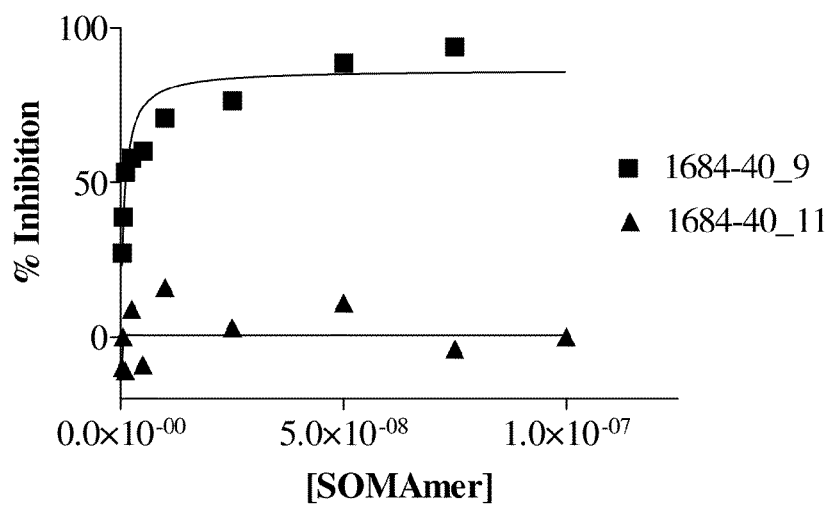

Base = Uridine (U) or Cytidine(C) (attachment is to the 5-position)
K = R' group plus $(CH_2)_n$ connecting group, where n = 0-3

*Denotes point of attachment of the R' group to $(CH_2)_n$ connecting group

FIG. 3 (continued)

wherein

R'''' is selected from the group consisting of a branched or linear lower alkyl (C1-C20); halogen (F, Cl, Br, I); nitrile (CN); boronic acid ($BO_2H_2$); carboxylic acid (COOH); carboxylic acid ester (COOR''); primary amide ($CONH_2$); secondary amide (CONHR''); tertiary amide (CONR''R'''); sulfonamide ($SO_2NH_2$); N-alkylsulfonamide (SONHR'').

wherein

R'', R''' are independently selected from a group consisting of a branched or linear lower alkyl (C1-C2)); phenyl ($C_6H_5$); an R'''' substituted phenyl ring (R''''$C_6H_4$); wherein R'''' is defined above; a carboxylic acid (COOH); a carboxylic acid ester (COOR''''); wherein R'''' is a branched or linear lower alkyl (C1-C20); and cycloalkyl; wherein R'' = R''' = $(CH_2)_n$; wherein n =2-10.

FIG. 8

| Aptamer Designation | Random Region Plus Fixed Sequence (lower case) 5'--->3' | Seq-ID No: |
|---|---|---|
| 1684-35 | cctgcaccagtgtcccGGAWGMAMMWWMWAWMWAWGWAGWGGMMMWMWAGGGWMWGgamggagaggaggamgg | 4 |
| 1684-36 | cctgcaccagtgtcccMWGWAMMMWMWAGMAWAMWWMGAWGMGGAWGWAWAMMMGGgamggagaggaggamgg | 5 |
| 1684-40 | cctgcaccagtgtcccMGAMGGGGMMMWMWAGMMGWAMWMWGWAAWGGMGGAWGMWgamggagaggaggaggamgg | 6 |
| 1684-44 | cctgcaccagtgtcccMMMMGMMMWMWAGMWWGMGGAWGMGGGWGAMGAGAMGMGgamggagaggaggamgg | 7 |
| 1684-51 | cctgcaccagtgtcccGGAWGMAWGGWMGAWAGGAWAMAAWGAMAMGMMMWMWAGGgamggagaggaggamgg | 8 |
| 1684-54 | cctgcaccagtgtcccGGAWGWGMGMGAGWMGMWMMMWMWAGGAAMAMGMWGAMMGgamggagaggaggamgg | 9 |
| 1684-55 | cctgcaccagtgtcccGAMGGGGMMMWMWAGMMGWAMWMWGWAAWGGMGGAWGMWgamggagaggaggamgg | 10 |
| 1684-61 | cctgcaccagtgtcccGMWWWAGGMGGAWGWWGAAAGAAGMWWAMMMWMWAGMMWAgamggagaggaggamgg | 11 |
| 1684-63 | cctgcaccagtgtcccGGMWWWGMMMWMWAGMGMMMGWAWWGMGMGGAWGMWAWGWgamggagaggaggamgg | 12 |
| 1684-64 | cctgcaccagtgtcccMWGMGGAWMWGGWGMMMWMWAGMWGGAWGAMMWGGAMMWGGgamggagaggaggamgg | 13 |

Lower Case = fixed region
Upper case = random region
W = TrpdU
M,m = methyl dC

FIG. 9A

A. Sequence Family

| | A | | B |
|---|---|---|---|
| *Consensus:* | CCCTCTAGX | | YCGGATGZ |

| SEQ ID NO. | | | | |
|---|---|---|---|---|
| 22 | CGACGGGG | CCCTCTAGC | CGTACTCTGTAATG | GCGGATGC T |
| 23 | GACGGGG | CCCTCTAGC | CGTACTCTGTAATG | CGGATGC T |
| 24 | GGCTTTG | CCCTCTAGC | GCCCGTATTGC | CGGATGC TATGT |
| 25 | CCCCG | CCCTCTAGC | TT | GCGGATGC GGGGTGACGAGACGCG |
| 26 | CTGGTG | CCCTCTAGC | TGGATGACCTGG-3' | |
| 27 | CTGTA | CCCTCTAGC | ATACTTCGAT | GCGGATGT ATACCCGG |
| 28 | GAAGCTTA | CCCTCTAGC | CTA-3' | |
| 29 | GCGCGAGTCGCT | CCCTCTAGG | AACACGCTGACCG-3' | 5'-ccGGATCT |
| 30 | ACCTTCTATCTATGTAGTGG | CCCTCTAGG | GTCTG-3' | 5'-ccGGATGC |
| 31 | ATGGTCGATAGGATACAATGACACG | CCCTCTAGG -3' | | 5'-ccGGATGC |
| 32 | | | | 5'-CT GCGGATGC GAT |
| 33 | | | | 5'-GCTTTAG GCGGATGT TGAAA |

*Notes: Sequences are shown 5' to 3'. (X = G or C), (Y = G or C), (Z = C or T). Lower case = fixed region sequence. T = TrpdU, C = MdC.*

FIG. 9B

Consensus Model

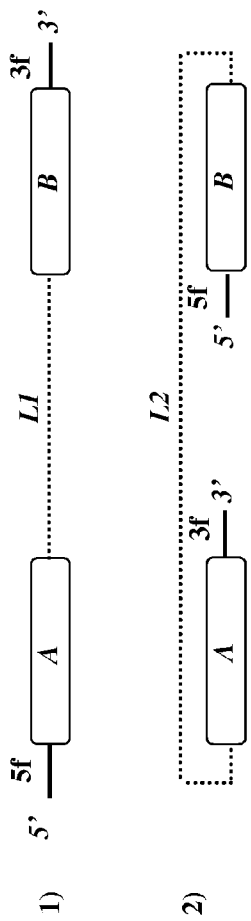

FIG. 10

Aptamer Consensus Sequence A

|   | 1 | 2 | 3 | 4 | 5 | 6 | 7 | 8 | 9 |
|---|---|---|---|---|---|---|---|---|---|
| A | 0 | 0 | 0 | 0 | 0 | 0 | 100 | 0 | 0 |
| W | 0 | 0 | 0 | 100 | 0 | 100 | 0 | 0 | 0 |
| G | 0 | 0 | 0 | 0 | 0 | 0 | 0 | 100 | 30 |
| C | 100 | 100 | 100 | 0 | 100 | 0 | 0 | 0 | 70 |

| Consensus A | C | C | C | W | C | W | A | G | X |
|---|---|---|---|---|---|---|---|---|---|

Aptamer Consensus Sequence B

|   | 1 | 2 | 3 | 4 | 5 | 6 | 7 | 8 |
|---|---|---|---|---|---|---|---|---|
| A | 0 | 0 | 0 | 0 | 100 | 0 | 0 | 0 |
| W | 0 | 0 | 0 | 0 | 0 | 100 | 0 | 30 |
| G | 70 | 0 | 100 | 100 | 0 | 0 | 100 | 0 |
| C | 30 | 100 | 0 | 0 | 0 | 0 | 0 | 70 |

| Consensus B | Y | C | G | G | A | W | G | Z |
|---|---|---|---|---|---|---|---|---|

Row (A) indicates the frequency at which A is observed in the 1684-40 aptamer family at each of the 9 or 8 conserved positions (of Consensus A or B respectively).

Row (W) indicates the frequency at which W is observed in the 1684-40 aptamer family at each of the 9 or 8 conserved positions (of Consensus A or B respectively).

Row (G) indicates the frequency at which G is observed in the 1684-40 aptamer family at each of the 9 or 8 conserved positions (of Consensus A or B respectively).

Row (C) indicates the frequency at which C is observed in the 1684-40 aptamer family at each of the 9 or 8 conserved positions (of Consensus A or B respectively)

Row (Consensus) is the consensus sequence for the aptamer with the TrpdU substitution, where:
  W = modified U
  C = modified C
  X = C or G
  Y = C or G

```
                             SEQUENCE LISTING

<160> NUMBER OF SEQ ID NOS: 33

<210> SEQ ID NO 1
<211> LENGTH: 73
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(56)
<223> OTHER INFORMATION: n is a, c, g, or t

<400> SEQUENCE: 1
ccgtcctcct ctccgtnnnn nnnnnnnnnn nnnnnnnnnn nnnnnnnnnn nnnnnnggga       60
cactgggtgc agg                                                         73

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2
atatatatcc tgcacccagt gtccc                                            25

<210> SEQ ID NO 3
<211> LENGTH: 25
<212> TYPE: DNA
<213> ORGANISM: Artificial Sequence
<220> FEATURE:
<223> OTHER INFORMATION: Synthetic

<400> SEQUENCE: 3 tttttttcc gtcctcctct ccgtc                                             25

<210> SEQ ID NO 4
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (21)..(21)
<223> OTHER INFORMATION: 5-methyl C
<220> FEATURE:
<221> NAME/KEY: misc_feature
<222> LOCATION: (23)..(23)
<223> OTHER INFORMATION: 5-tryptaminocarboxamide modified T
<220> FEATURE:
<221> NAME/KEY: misc_feature
<222> LOCATION: (25)..(26)
<223> OTHER INFORMATION: 5-tryptaminocarboxamide modified T
<220> FEATURE:
<221> NAME/KEY: misc_feature
<222> LOCATION: (27)..(28)
<223> OTHER INFORMATION: 5-methyl C
<220> FEATURE:
<221> NAME/KEY: misc_feature
<222> LOCATION: (29)..(29)
<223> OTHER INFORMATION: 5-tryptaminocarboxamide modified T
<220> FEATURE:
<221> NAME/KEY: misc_feature
<222> LOCATION: (30)..(30)
<223> OTHER INFORMATION: 5-methyl C
<220> FEATURE:
<221> NAME/KEY: misc_feature
<222> LOCATION: (32)..(32)
<223> OTHER INFORMATION: 5-methyl C
<220> FEATURE:
<221> NAME/KEY: misc_feature
<222> LOCATION: (33)..(33)
<223> OTHER INFORMATION: 5-tryptaminocarboxamide modified T
<220> FEATURE:
<221> NAME/KEY: misc_feature
<222> LOCATION: (34)..(34)
<223> OTHER INFORMATION: 5-methyl C
<220> FEATURE:
<221> NAME/KEY: misc_feature
<222> LOCATION: (36)..(36)
<223> OTHER INFORMATION: 5-methyl C
<220> FEATURE:
<221> NAME/KEY: misc_feature
<222> LOCATION: (38)..(38)
<223> OTHER INFORMATION: 5-methyl C
<220> FEATURE:
<221> NAME/KEY: misc_feature
<222> LOCATION: (41)..(41)
<223> OTHER INFORMATION: 5-methyl C
<220> FEATURE:
<221> NAME/KEY: misc_feature
<222> LOCATION: (44)..(46)
<223> OTHER INFORMATION: 5-tryptaminocarboxamide modified T
<220> FEATURE:
<221> NAME/KEY: misc_feature
<222> LOCATION: (47)..(47)
<223> OTHER INFORMATION: 5-methyl C
<220> FEATURE:
<221> NAME/KEY: misc_feature
<222> LOCATION: (48)..(48)
<223> OTHER INFORMATION: 5-tryptaminocarboxamide modified T
<220> FEATURE:
<221> NAME/KEY: misc_feature
<222> LOCATION: (49)..(49)
<223> OTHER INFORMATION: 5-methyl C
<220> FEATURE:
<221> NAME/KEY: misc_feature
<222> LOCATION: (54)..(54)
<223> OTHER INFORMATION: 5-methyl C
<220> FEATURE:
<221> NAME/KEY: misc_feature
<222> LOCATION: (55)..(55)
<223> OTHER INFORMATION: 5-tryptaminocarboxamide modified T
<220> FEATURE:
<221> NAME/KEY: misc_feature
<222> LOCATION: (56)..(56)
<223> OTHER INFORMATION: 5-methyl C
<220> FEATURE:
<221> NAME/KEY: misc_feature
<222> LOCATION: (60)..(60)
<223> OTHER INFORMATION: 5-tryptaminocarboxamide modified T
<220> FEATURE:
```

<221> NAME/KEY: misc_feature
<222> LOCATION: (72)..(72)
<223> OTHER INFORMATION: 5-tryptaminocarboxamide modified T

<400> SEQUENCE: 4
cctgcaccca gtgtcccgga ngnannnnnn annnangnag nggnnnnnna gggnnnggan    60
ggagaggagg angg                                                      74

<210> SEQ ID NO 5
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(18)
<223> OTHER INFORMATION: 5-methyl C
<220> FEATURE:
<221> NAME/KEY: misc_feature
<222> LOCATION: (19)..(19)
<223> OTHER INFORMATION: 5-tryptaminocarboxamide modified T
<220> FEATURE:
<221> NAME/KEY: misc_feature
<222> LOCATION: (21)..(21)
<223> OTHER INFORMATION: 5-tryptaminocarboxamide modified T
<220> FEATURE:
<221> NAME/KEY: misc_feature
<222> LOCATION: (23)..(25)
<223> OTHER INFORMATION: 5-methyl C
<220> FEATURE:
<221> NAME/KEY: misc_feature
<222> LOCATION: (26)..(26)
<223> OTHER INFORMATION: 5-tryptaminocarboxamide modified T
<220> FEATURE:
<221> NAME/KEY: misc_feature
<222> LOCATION: (27)..(27)
<223> OTHER INFORMATION: 5-methyl C
<220> FEATURE:
<221> NAME/KEY: misc_feature
<222> LOCATION: (28)..(28)
<223> OTHER INFORMATION: 5-tryptaminocarboxamide modified T
<220> FEATURE:
<221> NAME/KEY: misc_feature
<222> LOCATION: (31)..(31)
<223> OTHER INFORMATION: 5-methyl C
<220> FEATURE:
<221> NAME/KEY: misc_feature
<222> LOCATION: (33)..(33)
<223> OTHER INFORMATION: 5-tryptaminocarboxamide modified T
<220> FEATURE:
<221> NAME/KEY: misc_feature
<222> LOCATION: (35)..(35)
<223> OTHER INFORMATION: 5-methyl C
<220> FEATURE:
<221> NAME/KEY: misc_feature
<222> LOCATION: (36)..(37)
<223> OTHER INFORMATION: 5-tryptaminocarboxamide modified T
<220> FEATURE:
<221> NAME/KEY: misc_feature
<222> LOCATION: (38)..(38)
<223> OTHER INFORMATION: 5-methyl C
<220> FEATURE:
<221> NAME/KEY: misc_feature
<222> LOCATION: (41)..(41)
<223> OTHER INFORMATION: 5-tryptaminocarboxamide modified T
<220> FEATURE:
<221> NAME/KEY: misc_feature
<222> LOCATION: (43)..(43)
<223> OTHER INFORMATION: 5-methyl C
<220> FEATURE:
<221> NAME/KEY: misc_feature
<222> LOCATION: (47)..(47)
<223> OTHER INFORMATION: 5-tryptaminocarboxamide modified T
<220> FEATURE:
<221> NAME/KEY: misc_feature

```
<222> LOCATION: (49)..(49)
<223> OTHER INFORMATION: 5-tryptaminocarboxamide modified T
<220> FEATURE:
<221> NAME/KEY: misc_feature
<222> LOCATION: (51)..(51)
<223> OTHER INFORMATION: 5-tryptaminocarboxamide modified T
<220> FEATURE:
<221> NAME/KEY: misc_feature
<222> LOCATION: (53)..(55)
<223> OTHER INFORMATION: 5-methyl C
<220> FEATURE:
<221> NAME/KEY: misc_feature
<222> LOCATION: (60)..(60)
<223> OTHER INFORMATION: 5-methyl C
<220> FEATURE:
<221> NAME/KEY: misc_feature
<222> LOCATION: (72)..(72)
<223> OTHER INFORMATION: 5-methyl C

<400> SEQUENCE: 5
cctgcaccca gtgtcccnng nannnnnnag nanannnnga ngnggangna nannngggan      60
ggagaggagg angg                                                       74

<210> SEQ ID NO 6
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(18)
<223> OTHER INFORMATION: 5-methyl C
<220> FEATURE:
<221> NAME/KEY: misc_feature
<222> LOCATION: (21)..(21)
<223> OTHER INFORMATION: 5-methyl C
<220> FEATURE:
<221> NAME/KEY: misc_feature
<222> LOCATION: (26)..(28)
<223> OTHER INFORMATION: 5-methyl C
<220> FEATURE:
<221> NAME/KEY: misc_feature
<222> LOCATION: (29)..(29)
<223> OTHER INFORMATION: 5-tryptaminocarboxamide modified T
<220> FEATURE:
<221> NAME/KEY: misc_feature
<222> LOCATION: (30)..(30)
<223> OTHER INFORMATION: 5-methyl C
<220> FEATURE:
<221> NAME/KEY: misc_feature
<222> LOCATION: (31)..(31)
<223> OTHER INFORMATION: 5-tryptaminocarboxamide modified T
<220> FEATURE:
<221> NAME/KEY: misc_feature
<222> LOCATION: (34)..(35)
<223> OTHER INFORMATION: 5-methyl C
<220> FEATURE:
<221> NAME/KEY: misc_feature
<222> LOCATION: (37)..(37)
<223> OTHER INFORMATION: 5-tryptaminocarboxamide modified T
<220> FEATURE:
<221> NAME/KEY: misc_feature
<222> LOCATION: (39)..(39)
<223> OTHER INFORMATION: 5-methyl C
<220> FEATURE:
<221> NAME/KEY: misc_feature
<222> LOCATION: (40)..(40)
<223> OTHER INFORMATION: 5-tryptaminocarboxamide modified T
<220> FEATURE:
<221> NAME/KEY: misc_feature
<222> LOCATION: (41)..(41)
<223> OTHER INFORMATION: 5-methyl C
<220> FEATURE:
<221> NAME/KEY: misc_feature
<222> LOCATION: (42)..(42)
```

<223> OTHER INFORMATION: 5-tryptaminocarboxamide modified T
<220> FEATURE:
<221> NAME/KEY: misc_feature
<222> LOCATION: (44)..(44)
<223> OTHER INFORMATION: 5-tryptaminocarboxamide modified T
<220> FEATURE:
<221> NAME/KEY: misc_feature
<222> LOCATION: (47)..(47)
<223> OTHER INFORMATION: 5-tryptaminocarboxamide modified T
<220> FEATURE:
<221> NAME/KEY: misc_feature
<222> LOCATION: (50)..(50)
<223> OTHER INFORMATION: 5-methyl C
<220> FEATURE:
<221> NAME/KEY: misc_feature
<222> LOCATION: (54)..(54)
<223> OTHER INFORMATION: 5-tryptaminocarboxamide modified T
<220> FEATURE:
<221> NAME/KEY: misc_feature
<222> LOCATION: (56)..(56)
<223> OTHER INFORMATION: 5-methyl C
<220> FEATURE:
<221> NAME/KEY: misc_feature
<222> LOCATION: (57)..(57)
<223> OTHER INFORMATION: 5-tryptaminocarboxamide modified T
<220> FEATURE:
<221> NAME/KEY: misc_feature
<222> LOCATION: (60)..(60)
<223> OTHER INFORMATION: 5-methyl C
<220> FEATURE:
<221> NAME/KEY: misc_feature
<222> LOCATION: (72)..(72)
<223> OTHER INFORMATION: 5-methyl C

<400> SEQUENCE: 6
cctgcaccca gtgtcccnga ngggngnnnnn nagnngnann nngnaanggn ggangnngan    60
ggagaggagg angg    74

<210> SEQ ID NO 7
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(21)
<223> OTHER INFORMATION: 5-methyl C
<220> FEATURE:
<221> NAME/KEY: misc_feature
<222> LOCATION: (23)..(25)
<223> OTHER INFORMATION: 5-methyl C
<220> FEATURE:
<221> NAME/KEY: misc_feature
<222> LOCATION: (26)..(26)
<223> OTHER INFORMATION: 5-tryptaminocarboxamide modified T
<220> FEATURE:
<221> NAME/KEY: misc_feature
<222> LOCATION: (27)..(27)
<223> OTHER INFORMATION: 5-methyl C
<220> FEATURE:
<221> NAME/KEY: misc_feature
<222> LOCATION: (28)..(28)
<223> OTHER INFORMATION: 5-tryptaminocarboxamide modified T
<220> FEATURE:
<221> NAME/KEY: misc_feature
<222> LOCATION: (31)..(31)
<223> OTHER INFORMATION: 5-methyl C
<220> FEATURE:
<221> NAME/KEY: misc_feature
<222> LOCATION: (32)..(33)
<223> OTHER INFORMATION: 5-tryptaminocarboxamide modified T
<220> FEATURE:
<221> NAME/KEY: misc_feature
<222> LOCATION: (35)..(35)
<223> OTHER INFORMATION: 5-methyl C

```
<220> FEATURE:
<221> NAME/KEY: misc_feature
<222> LOCATION: (39)..(39)
<223> OTHER INFORMATION: 5-tryptaminocarboxamide modified T
<220> FEATURE:
<221> NAME/KEY: misc_feature
<222> LOCATION: (41)..(41)
<223> OTHER INFORMATION: 5-methyl C
<220> FEATURE:
<221> NAME/KEY: misc_feature
<222> LOCATION: (46)..(46)
<223> OTHER INFORMATION: 5-tryptaminocarboxamide modified T
<220> FEATURE:
<221> NAME/KEY: misc_feature
<222> LOCATION: (49)..(49)
<223> OTHER INFORMATION: 5-methyl C
<220> FEATURE:
<221> NAME/KEY: misc_feature
<222> LOCATION: (54)..(54)
<223> OTHER INFORMATION: 5-methyl C
<220> FEATURE:
<221> NAME/KEY: misc_feature
<222> LOCATION: (56)..(56)
<223> OTHER INFORMATION: 5-methyl C
<220> FEATURE:
<221> NAME/KEY: misc_feature
<222> LOCATION: (60)..(60)
<223> OTHER INFORMATION: 5-methyl C
<220> FEATURE:
<221> NAME/KEY: misc_feature
<222> LOCATION: (72)..(72)
<223> OTHER INFORMATION: 5-methyl C

<400> SEQUENCE: 7
cctgcaccca gtgtcccnnn ngnnnnnnag nnngnggang ngggngang agangnggan      60 ggagaggagg angg                                                      74

<210> SEQ ID NO 8
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: 5-tryptaminocarboxamide modified T
<220> FEATURE:
<221> NAME/KEY: misc_feature
<222> LOCATION: (23)..(23)
<223> OTHER INFORMATION: 5-methyl C
<220> FEATURE:
<221> NAME/KEY: misc_feature
<222> LOCATION: (25)..(25)
<223> OTHER INFORMATION: 5-tryptaminocarboxamide modified T
<220> FEATURE:
<221> NAME/KEY: misc_feature
<222> LOCATION: (28)..(28)
<223> OTHER INFORMATION: 5-tryptaminocarboxamide modified T
<220> FEATURE:
<221> NAME/KEY: misc_feature
<222> LOCATION: (29)..(29)
<223> OTHER INFORMATION: 5-methyl C
<220> FEATURE:
<221> NAME/KEY: misc_feature
<222> LOCATION: (32)..(32)
<223> OTHER INFORMATION: 5-tryptaminocarboxamide modified T
<220> FEATURE:
<221> NAME/KEY: misc_feature
<222> LOCATION: (37)..(37)
<223> OTHER INFORMATION: 5-tryptaminocarboxamide modified T
<220> FEATURE:
<221> NAME/KEY: misc_feature
<222> LOCATION: (39)..(39)
<223> OTHER INFORMATION: 5-methyl C
<220> FEATURE:
```

```
<221> NAME/KEY: misc_feature
<222> LOCATION: (42)..(42)
<223> OTHER INFORMATION: 5-tryptaminocarboxamide modified T
<220> FEATURE:
<221> NAME/KEY: misc_feature
<222> LOCATION: (45)..(45)
<223> OTHER INFORMATION: 5-methyl C
<220> FEATURE:
<221> NAME/KEY: misc_feature
<222> LOCATION: (47)..(47)
<223> OTHER INFORMATION: 5-methyl C
<220> FEATURE:
<221> NAME/KEY: misc_feature
<222> LOCATION: (49)..(51)
<223> OTHER INFORMATION: 5-methyl C
<220> FEATURE:
<221> NAME/KEY: misc_feature
<222> LOCATION: (52)..(52)
<223> OTHER INFORMATION: 5-tryptaminocarboxamide modified T
<220> FEATURE:
<221> NAME/KEY: misc_feature
<222> LOCATION: (53)..(53)
<223> OTHER INFORMATION: 5-methyl C
<220> FEATURE:
<221> NAME/KEY: misc_feature
<222> LOCATION: (54)..(54)
<223> OTHER INFORMATION: 5-tryptaminocarboxamide modified T
<220> FEATURE:
<221> NAME/KEY: misc_feature
<222> LOCATION: (60)..(60)
<223> OTHER INFORMATION: 5-methyl C
<220> FEATURE:
<221> NAME/KEY: misc_feature
<222> LOCATION: (72)..(72)
<223> OTHER INFORMATION: 5-methyl C

<400> SEQUENCE: 8
cctgcaccca gtgtcccgga ngnanggnng anagganana anganangnn nnnnagggan    60
ggagaggagg angg                                                      74

<210> SEQ ID NO 9
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: 5-trytaminocarboxamide modified T
<220> FEATURE:
<221> NAME/KEY: misc_feature
<222> LOCATION: (23)..(23)
<223> OTHER INFORMATION: 5-trytaminocarboxamide modified T
<220> FEATURE:
<221> NAME/KEY: misc_feature
<222> LOCATION: (25)..(25)
<223> OTHER INFORMATION: 5-methyl C
<220> FEATURE:
<221> NAME/KEY: misc_feature
<222> LOCATION: (27)..(27)
<223> OTHER INFORMATION: 5-methyl C
<220> FEATURE:
<221> NAME/KEY: misc_feature
<222> LOCATION: (31)..(31)
<223> OTHER INFORMATION: 5-trytaminocarboxamide modified T
<220> FEATURE:
<221> NAME/KEY: misc_feature
<222> LOCATION: (32)..(32)
<223> OTHER INFORMATION: 5-methyl C
<220> FEATURE:
<221> NAME/KEY: misc_feature
<222> LOCATION: (34)..(34)
<223> OTHER INFORMATION: 5-methyl C
<220> FEATURE:
<221> NAME/KEY: misc_feature
```

<222> LOCATION: (35)..(35)
<223> OTHER INFORMATION: 5-trytaminocarboxamide modified T
<220> FEATURE:
<221> NAME/KEY: misc_feature
<222> LOCATION: (36)..(38)
<223> OTHER INFORMATION: 5-methyl C
<220> FEATURE:
<221> NAME/KEY: misc_feature
<222> LOCATION: (39)..(39)
<223> OTHER INFORMATION: 5-trytaminocarboxamide modified T
<220> FEATURE:
<221> NAME/KEY: misc_feature
<222> LOCATION: (40)..(40)
<223> OTHER INFORMATION: 5-methyl C
<220> FEATURE:
<221> NAME/KEY: misc_feature
<222> LOCATION: (41)..(41)
<223> OTHER INFORMATION: 5-trytaminocarboxamide modified T
<220> FEATURE:
<221> NAME/KEY: misc_feature
<222> LOCATION: (47)..(47)
<223> OTHER INFORMATION: 5-methyl C
<220> FEATURE:
<221> NAME/KEY: misc_feature
<222> LOCATION: (49)..(49)
<223> OTHER INFORMATION: 5-methyl C
<220> FEATURE:
<221> NAME/KEY: misc_feature
<222> LOCATION: (51)..(51)
<223> OTHER INFORMATION: 5-methyl C
<220> FEATURE:
<221> NAME/KEY: misc_feature
<222> LOCATION: (52)..(52)
<223> OTHER INFORMATION: 5-trytaminocarboxamide modified T
<220> FEATURE:
<221> NAME/KEY: misc_feature
<222> LOCATION: (55)..(56)
<223> OTHER INFORMATION: 5-methyl C
<220> FEATURE:
<221> NAME/KEY: misc_feature
<222> LOCATION: (60)..(60)
<223> OTHER INFORMATION: 5-methyl C
<220> FEATURE:
<221> NAME/KEY: misc_feature
<222> LOCATION: (72)..(72)
<223> OTHER INFORMATION: 5-methyl C

<400> SEQUENCE: 9
cctgcaccca gtgtcccgga ngngngngag nngnnnnnnn naggaanang nngannggan    60
ggagaggagg angg                                                     74

<210> SEQ ID NO 10
<211> LENGTH: 73
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: 5-methyl C
<220> FEATURE:
<221> NAME/KEY: misc_feature
<222> LOCATION: (25)..(27)
<223> OTHER INFORMATION: 5-methyl C
<220> FEATURE:
<221> NAME/KEY: misc_feature
<222> LOCATION: (28)..(28)
<223> OTHER INFORMATION: 5-tryptaminocarboxamide modified T
<220> FEATURE:
<221> NAME/KEY: misc_feature
<222> LOCATION: (29)..(29)
<223> OTHER INFORMATION: 5-methyl C
<220> FEATURE:
<221> NAME/KEY: misc_feature
<222> LOCATION: (30)..(30)

```
<223> OTHER INFORMATION: 5-tryptaminocarboxamide modified T
<220> FEATURE:
<221> NAME/KEY: misc_feature
<222> LOCATION: (33)..(34)
<223> OTHER INFORMATION: 5-methyl C
<220> FEATURE:
<221> NAME/KEY: misc_feature
<222> LOCATION: (36)..(36)
<223> OTHER INFORMATION: 5-tryptaminocarboxamide modified T
<220> FEATURE:
<221> NAME/KEY: misc_feature
<222> LOCATION: (38)..(38)
<223> OTHER INFORMATION: 5-methyl C
<220> FEATURE:
<221> NAME/KEY: misc_feature
<222> LOCATION: (39)..(39)
<223> OTHER INFORMATION: 5-tryptaminocarboxamide modified T
<220> FEATURE:
<221> NAME/KEY: misc_feature
<222> LOCATION: (40)..(40)
<223> OTHER INFORMATION: 5-methyl C
<220> FEATURE:
<221> NAME/KEY: misc_feature
<222> LOCATION: (41)..(41)
<223> OTHER INFORMATION: 5-tryptaminocarboxamide modified T
<220> FEATURE:
<221> NAME/KEY: misc_feature
<222> LOCATION: (43)..(43)
<223> OTHER INFORMATION: 5-tryptaminocarboxamide modified T
<220> FEATURE:
<221> NAME/KEY: misc_feature
<222> LOCATION: (46)..(46)
<223> OTHER INFORMATION: 5-tryptaminocarboxamide modified T
<220> FEATURE:
<221> NAME/KEY: misc_feature
<222> LOCATION: (49)..(49)
<223> OTHER INFORMATION: 5-methyl C
<220> FEATURE:
<221> NAME/KEY: misc_feature
<222> LOCATION: (53)..(53)
<223> OTHER INFORMATION: 5-tryptaminocarboxamide modified T
<220> FEATURE:
<221> NAME/KEY: misc_feature
<222> LOCATION: (55)..(55)
<223> OTHER INFORMATION: 5-methyl C
<220> FEATURE:
<221> NAME/KEY: misc_feature
<222> LOCATION: (56)..(56)
<223> OTHER INFORMATION: 5-tryptaminocarboxamide modified T
<220> FEATURE:
<221> NAME/KEY: misc_feature
<222> LOCATION: (59)..(59)
<223> OTHER INFORMATION: 5-methyl C
<220> FEATURE:
<221> NAME/KEY: misc_feature
<222> LOCATION: (71)..(71)
<223> OTHER INFORMATION: 5-methyl C

<400> SEQUENCE: 10
cctgcaccca gtgtcccgan ggggnnnnnn agnngnannn ngnaanggng gangnngang    60
gagaggagga ngg                                                      73

<210> SEQ ID NO 11
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(19)
<223> OTHER INFORMATION: 5-methyl C
<220> FEATURE:
<221> NAME/KEY: misc_feature
<222> LOCATION: (20)..(22)
<223> OTHER INFORMATION: 5-tryptaminocarboxamide modified T
```

```
<220> FEATURE:
<221> NAME/KEY: misc_feature
<222> LOCATION: (26)..(26)
<223> OTHER INFORMATION: 5-methyl C
<220> FEATURE:
<221> NAME/KEY: misc_feature
<222> LOCATION: (30)..(30)
<223> OTHER INFORMATION: 5-tryptaminocarboxamide modified T
<220> FEATURE:
<221> NAME/KEY: misc_feature
<222> LOCATION: (32)..(33)
<223> OTHER INFORMATION: 5-tryptaminocarboxamide modified T
<220> FEATURE:
<221> NAME/KEY: misc_feature
<222> LOCATION: (42)..(42)
<223> OTHER INFORMATION: 5-methyl C
<220> FEATURE:
<221> NAME/KEY: misc_feature
<222> LOCATION: (43)..(44)
<223> OTHER INFORMATION: 5-tryptaminocarboxamide modified T
<220> FEATURE:
<221> NAME/KEY: misc_feature
<222> LOCATION: (46)..(48)
<223> OTHER INFORMATION: 5-methyl C
<220> FEATURE:
<221> NAME/KEY: misc_feature
<222> LOCATION: (49)..(49)
<223> OTHER INFORMATION: 5-tryptaminocarboxamide modified T
<220> FEATURE:
<221> NAME/KEY: misc_feature
<222> LOCATION: (50)..(50)
<223> OTHER INFORMATION: 5-methyl C
<220> FEATURE:
<221> NAME/KEY: misc_feature
<222> LOCATION: (51)..(51)
<223> OTHER INFORMATION: 5-tryptaminocarboxamide modified T
<220> FEATURE:
<221> NAME/KEY: misc_feature
<222> LOCATION: (54)..(55)
<223> OTHER INFORMATION: 5-methyl C
<220> FEATURE:
<221> NAME/KEY: misc_feature
<222> LOCATION: (56)..(56)
<223> OTHER INFORMATION: 5-tryptaminocarboxamide modified T
<220> FEATURE:
<221> NAME/KEY: misc_feature
<222> LOCATION: (60)..(60)
<223> OTHER INFORMATION: 5-methyl C
<220> FEATURE:
<221> NAME/KEY: misc_feature
<222> LOCATION: (72)..(72)
<223> OTHER INFORMATION: 5-methyl C

<400> SEQUENCE: 11
cctgcaccca gtgtcccgnn nnaggnggan gnngaaagaa gnnnannnnn nagnnnagan    60
ggagaggagg angg                                                     74

<210> SEQ ID NO 12
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: 5-methyl C
<220> FEATURE:
<221> NAME/KEY: misc_feature
<222> LOCATION: (21)..(23)
<223> OTHER INFORMATION: 5-tryptaminocarboxamide modified T
<220> FEATURE:
<221> NAME/KEY: misc_feature
<222> LOCATION: (25)..(27)
<223> OTHER INFORMATION: 5-methyl C
<220> FEATURE:
```

<221> NAME/KEY: misc_feature
<222> LOCATION: (28)..(28)
<223> OTHER INFORMATION: 5-tryptaminocarboxamide modified T
<220> FEATURE:
<221> NAME/KEY: misc_feature
<222> LOCATION: (29)..(29)
<223> OTHER INFORMATION: 5-methyl C
<220> FEATURE:
<221> NAME/KEY: misc_feature
<222> LOCATION: (30)..(30)
<223> OTHER INFORMATION: 5-tryptaminocarboxamide modified T
<220> FEATURE:
<221> NAME/KEY: misc_feature
<222> LOCATION: (33)..(33)
<223> OTHER INFORMATION: 5-methyl C
<220> FEATURE:
<221> NAME/KEY: misc_feature
<222> LOCATION: (35)..(37)
<223> OTHER INFORMATION: 5-methyl C
<220> FEATURE:
<221> NAME/KEY: misc_feature
<222> LOCATION: (39)..(39)
<223> OTHER INFORMATION: 5-tryptaminocarboxamide modified T
<220> FEATURE:
<221> NAME/KEY: misc_feature
<222> LOCATION: (41)..(42)
<223> OTHER INFORMATION: 5-tryptaminocarboxamide modified T
<220> FEATURE:
<221> NAME/KEY: misc_feature
<222> LOCATION: (44)..(44)
<223> OTHER INFORMATION: 5-methyl C
<220> FEATURE:
<221> NAME/KEY: misc_feature
<222> LOCATION: (46)..(46)
<223> OTHER INFORMATION: 5-methyl C
<220> FEATURE:
<221> NAME/KEY: misc_feature
<222> LOCATION: (50)..(50)
<223> OTHER INFORMATION: 5-tryptaminocarboxamide modified T
<220> FEATURE:
<221> NAME/KEY: misc_feature
<222> LOCATION: (52)..(52)
<223> OTHER INFORMATION: 5-methyl C
<220> FEATURE:
<221> NAME/KEY: misc_feature
<222> LOCATION: (53)..(53)
<223> OTHER INFORMATION: 5-tryptaminocarboxamide modified T
<220> FEATURE:
<221> NAME/KEY: misc_feature
<222> LOCATION: (55)..(55)
<223> OTHER INFORMATION: 5-tryptaminocarboxamide modified T
<220> FEATURE:
<221> NAME/KEY: misc_feature
<222> LOCATION: (57)..(57)
<223> OTHER INFORMATION: 5-tryptaminocarboxamide modified T
<220> FEATURE:
<221> NAME/KEY: misc_feature
<222> LOCATION: (60)..(60)
<223> OTHER INFORMATION: 5-methyl C
<220> FEATURE:
<221> NAME/KEY: misc_feature
<222> LOCATION: (72)..(72)
<223> OTHER INFORMATION: 5-methyl C

<400> SEQUENCE: 12
cctgcaccca gtgtcccggn nnngnnnnnn agngnnngna nngngnggan gnnangngan    60
ggagaggagg angg                                                      74

<210> SEQ ID NO 13
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: misc_feature

```
<222> LOCATION: (18)..(18)
<223> OTHER INFORMATION: 5-methyl C
<220> FEATURE:
<221> NAME/KEY: misc_feature
<222> LOCATION: (19)..(19)
<223> OTHER INFORMATION: 5-tryptaminocarboxamide modified T
<220> FEATURE:
<221> NAME/KEY: misc_feature
<222> LOCATION: (21)..(21)
<223> OTHER INFORMATION: 5-methyl C
<220> FEATURE:
<221> NAME/KEY: misc_feature
<222> LOCATION: (25)..(25)
<223> OTHER INFORMATION: 5-tryptaminocarboxamide modified T
<220> FEATURE:
<221> NAME/KEY: misc_feature
<222> LOCATION: (27)..(27)
<223> OTHER INFORMATION: 5-methyl C
<220> FEATURE:
<221> NAME/KEY: misc_feature
<222> LOCATION: (30)..(30)
<223> OTHER INFORMATION: 5-tryptaminocarboxamide modified T
<220> FEATURE:
<221> NAME/KEY: misc_feature
<222> LOCATION: (31)..(31)
<223> OTHER INFORMATION: 5-methyl C
<220> FEATURE:
<221> NAME/KEY: misc_feature
<222> LOCATION: (32)..(32)
<223> OTHER INFORMATION: 5-tryptaminocarboxamide modified T
<220> FEATURE:
<221> NAME/KEY: misc_feature
<222> LOCATION: (35)..(35)
<223> OTHER INFORMATION: 5-tryptaminocarboxamide modified T
<220> FEATURE:
<221> NAME/KEY: misc_feature
<222> LOCATION: (37)..(39)
<223> OTHER INFORMATION: 5-methyl C
<220> FEATURE:
<221> NAME/KEY: misc_feature
<222> LOCATION: (40)..(40)
<223> OTHER INFORMATION: 5-tryptaminocarboxamide modified T
<220> FEATURE:
<221> NAME/KEY: misc_feature
<222> LOCATION: (41)..(41)
<223> OTHER INFORMATION: 5-methyl C
<220> FEATURE:
<221> NAME/KEY: misc_feature
<222> LOCATION: (42)..(42)
<223> OTHER INFORMATION: 5-tryptaminocarboxamide modified T
<220> FEATURE:
<221> NAME/KEY: misc_feature
<222> LOCATION: (45)..(45)
<223> OTHER INFORMATION: 5-methyl C
<220> FEATURE:
<221> NAME/KEY: misc_feature
<222> LOCATION: (46)..(46)
<223> OTHER INFORMATION: 5-tryptaminocarboxamide modified T
<220> FEATURE:
<221> NAME/KEY: misc_feature
<222> LOCATION: (50)..(50)
<223> OTHER INFORMATION: 5-tryptaminocarboxamide modified T
<220> FEATURE:
<221> NAME/KEY: misc_feature
<222> LOCATION: (53)..(54)
<223> OTHER INFORMATION: 5-methyl C
<220> FEATURE:
<221> NAME/KEY: misc_feature
<222> LOCATION: (55)..(55)
<223> OTHER INFORMATION: 5-tryptaminocarboxamide modified T
<220> FEATURE:
<221> NAME/KEY: misc_feature
<222> LOCATION: (60)..(60)
<223> OTHER INFORMATION: 5-methyl C
<220> FEATURE:
<221> NAME/KEY: misc_feature
<222> LOCATION: (72)..(72)
<223> OTHER INFORMATION: 5-methyl C
```

<400> SEQUENCE: 13
cctgcaccca gtgtcccnng nggangngan nnggngnnnn nnagnnggan gannngggan      60
ggagaggagg angg                                                       74

<210> SEQ ID NO 14
<211> LENGTH: 317
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(100)
<223> OTHER INFORMATION: a nucleotide (N), a modified nucleotide, a
      spacer, or a combination thereof; may be absent
<220> FEATURE:
<221> NAME/KEY: misc_feature
<222> LOCATION: (101)..(103)
<223> OTHER INFORMATION: modified C
<220> FEATURE:
<221> NAME/KEY: misc_feature
<222> LOCATION: (104)..(104)
<223> OTHER INFORMATION: a modified nucleotide
<220> FEATURE:
<221> NAME/KEY: misc_feature
<222> LOCATION: (105)..(105)
<223> OTHER INFORMATION: modified C
<220> FEATURE:
<221> NAME/KEY: misc_feature
<222> LOCATION: (106)..(106)
<223> OTHER INFORMATION: a modified nucleotide
<220> FEATURE:
<221> NAME/KEY: misc_feature
<222> LOCATION: (110)..(209)
<223> OTHER INFORMATION: a nucleotide (N), a modified nucleotide, a
      spacer, or a combination thereof; may be absent
<220> FEATURE:
<221> NAME/KEY: misc_feature
<222> LOCATION: (211)..(211)
<223> OTHER INFORMATION: modified C
<220> FEATURE:
<221> NAME/KEY: misc_feature
<222> LOCATION: (215)..(215)
<223> OTHER INFORMATION: a modified nucleotide
<220> FEATURE:
<221> NAME/KEY: misc_feature
<222> LOCATION: (217)..(217)
<223> OTHER INFORMATION: C or a modified nucleotide
<220> FEATURE:
<221> NAME/KEY: misc_feature
<222> LOCATION: (218)..(317)
<223> OTHER INFORMATION: a nucleotide (N), a modified nucleotide, a
      spacer, or a combination thereof; may be absent

<400> SEQUENCE: 14
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnagsn nnnnnnnnnn     120 nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnns nggangnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnn                                                    317

<210> SEQ ID NO 15
<211> LENGTH: 317
<212> TYPE: DNA
<213> ORGANISM: Artificial Sequence
<220> FEATURE:
<223> OTHER INFORMATION: Synthetic
<220> FEATURE:

```
<221> NAME/KEY: misc_feature
<222> LOCATION: (1)..(100)
<223> OTHER INFORMATION: a nucleotide (N), a modified nucleotide, a
      spacer, or a combination thereof; may be absent
<220> FEATURE:
<221> NAME/KEY: misc_feature
<222> LOCATION: (101)..(101)
<223> OTHER INFORMATION: C or a modified nucleotide
<220> FEATURE:
<221> NAME/KEY: misc_feature
<222> LOCATION: (103)..(103)
<223> OTHER INFORMATION: a modified nucleotide
<220> FEATURE:
<221> NAME/KEY: misc_feature
<222> LOCATION: (107)..(107)
<223> OTHER INFORMATION: modified C
<220> FEATURE:
<221> NAME/KEY: misc_feature
<222> LOCATION: (109)..(208)
<223> OTHER INFORMATION: a nucleotide (N), a modified nucleotide, a
      spacer, or a combination thereof; may be absent
<220> FEATURE:
<221> NAME/KEY: misc_feature
<222> LOCATION: (212)..(212)
<223> OTHER INFORMATION: a modified nucleotide
<220> FEATURE:
<221> NAME/KEY: misc_feature
<222> LOCATION: (213)..(213)
<223> OTHER INFORMATION: modified C
<220> FEATURE:
<221> NAME/KEY: misc_feature
<222> LOCATION: (214)..(214)
<223> OTHER INFORMATION: a modified nucleotide
<220> FEATURE:
<221> NAME/KEY: misc_feature
<222> LOCATION: (215)..(217)
<223> OTHER INFORMATION: modified C
<220> FEATURE:
<221> NAME/KEY: misc_feature
<222> LOCATION: (218)..(317)
<223> OTHER INFORMATION: a nucleotide (N), a modified nucleotide, a
      spacer, or a combination thereof; may be absent

<400> SEQUENCE: 15
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn ngnaggnsnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnsg annnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnn                                                    317

<210> SEQ ID NO 16
<211> LENGTH: 317
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(100)
<223> OTHER INFORMATION: a nucleotide (N), a modified nucleotide, a
      spacer, or a combination thereof; may be absent
<220> FEATURE:
<221> NAME/KEY: misc_feature
<222> LOCATION: (101)..(103)
<223> OTHER INFORMATION: 5-methyl-2'-deoxycytidine
<220> FEATURE:
<221> NAME/KEY: misc_feature
<222> LOCATION: (104)..(104)
<223> OTHER INFORMATION: 5-(N-tryptaminocarboxyamide)-2'-deoxyuridine
<220> FEATURE:
<221> NAME/KEY: misc_feature
```

```
<222> LOCATION: (105)..(105)
<223> OTHER INFORMATION: 5-methyl-2'-deoxycytidine
<220> FEATURE:
<221> NAME/KEY: misc_feature
<222> LOCATION: (106)..(106)
<223> OTHER INFORMATION: 5-(N-tryptaminocarboxyamide)-2'-deoxyuridine
<220> FEATURE:
<221> NAME/KEY: misc_feature
<222> LOCATION: (110)..(209)
<223> OTHER INFORMATION: a nucleotide (N), a modified nucleotide, a
      spacer, or a combination thereof; may be absent
<220> FEATURE:
<221> NAME/KEY: misc_feature
<222> LOCATION: (211)..(211)
<223> OTHER INFORMATION: 5-methyl-2'-deoxycytidine
<220> FEATURE:
<221> NAME/KEY: misc_feature
<222> LOCATION: (215)..(215)
<223> OTHER INFORMATION: 5-(N-tryptaminocarboxyamide)-2'-deoxyuridine
<220> FEATURE:
<221> NAME/KEY: misc_feature
<222> LOCATION: (217)..(217)
<223> OTHER INFORMATION: C or a modified nucleotide
<220> FEATURE:
<221> NAME/KEY: misc_feature
<222> LOCATION: (218)..(317)
<223> OTHER INFORMATION: a nucleotide (N), a modified nucleotide, a
      spacer, or a combination thereof; may be absent

<400> SEQUENCE: 16
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnagsn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnns nggangnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnn                                                    317

<210> SEQ ID NO 17
<211> LENGTH: 317
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(100)
<223> OTHER INFORMATION: a nucleotide (N), a modified nucleotide, a
      spacer, or a combination thereof; may be absent
<220> FEATURE:
<221> NAME/KEY: misc_feature
<222> LOCATION: (101)..(101)
<223> OTHER INFORMATION: C or a modified nucleotide
<220> FEATURE:
<221> NAME/KEY: misc_feature
<222> LOCATION: (103)..(103)
<223> OTHER INFORMATION: 5-(N-tryptaminocarboxyamide)-2'-deoxyuridine
<220> FEATURE:
<221> NAME/KEY: misc_feature
<222> LOCATION: (107)..(107)
<223> OTHER INFORMATION: 5-methyl-2'-deoxycytidine
<220> FEATURE:
<221> NAME/KEY: misc_feature
<222> LOCATION: (109)..(208)
<223> OTHER INFORMATION: a nucleotide (N), a modified nucleotide, a
      spacer, or a combination thereof; may be absent
<220> FEATURE:
<221> NAME/KEY: misc_feature
<222> LOCATION: (212)..(212)
<223> OTHER INFORMATION: 5-(N-tryptaminocarboxyamide)-2'-deoxyuridine
<220> FEATURE:
<221> NAME/KEY: misc_feature
<222> LOCATION: (213)..(213)
```

```
<223> OTHER INFORMATION: 5-methyl-2'-deoxycytidine
<220> FEATURE:
<221> NAME/KEY: misc_feature
<222> LOCATION: (214)..(214)
<223> OTHER INFORMATION: 5-(N-tryptaminocarboxyamide)-2'-deoxyuridine
<220> FEATURE:
<221> NAME/KEY: misc_feature
<222> LOCATION: (215)..(217)
<223> OTHER INFORMATION: 5-methyl-2'-deoxycytidine
<220> FEATURE:
<221> NAME/KEY: misc_feature
<222> LOCATION: (218)..(317)
<223> OTHER INFORMATION: a nucleotide (N), a modified nucleotide, a
      spacer, or a combination thereof; may be absent

<400> SEQUENCE: 17
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn ngnaggnsnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnsg annnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnn                                                    317

<210> SEQ ID NO 18
<211> LENGTH: 117
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 5-methyl-2'-deoxycytidine
<220> FEATURE:
<221> NAME/KEY: misc_feature
<222> LOCATION: (4)..(4)
<223> OTHER INFORMATION: 5-(N-tryptaminocarboxyamide)-2'-deoxyuridine
<220> FEATURE:
<221> NAME/KEY: misc_feature
<222> LOCATION: (5)..(5)
<223> OTHER INFORMATION: 5-methyl-2'-deoxycytidine
<220> FEATURE:
<221> NAME/KEY: misc_feature
<222> LOCATION: (6)..(6)
<223> OTHER INFORMATION: 5-(N-tryptaminocarboxyamide)-2'-deoxyuridine
<220> FEATURE:
<221> NAME/KEY: misc_feature
<222> LOCATION: (10)..(109)
<223> OTHER INFORMATION: any naturally occurring or modified nucleotide;
      may be absent
<220> FEATURE:
<221> NAME/KEY: misc_feature
<222> LOCATION: (111)..(111)
<223> OTHER INFORMATION: 5-methyl-2'-deoxycytidine
<220> FEATURE:
<221> NAME/KEY: misc_feature
<222> LOCATION: (115)..(115)
<223> OTHER INFORMATION: 5-(N-tryptaminocarboxyamide)-2'-deoxyuridine
<220> FEATURE:
<221> NAME/KEY: misc_feature
<222> LOCATION: (117)..(117)
<223> OTHER INFORMATION: C or a modified nucleotide

<400> SEQUENCE: 18
nnnnnnagsn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnns nggangn         117

<210> SEQ ID NO 19
<211> LENGTH: 117
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: C or a modified nucleotide
<220> FEATURE:
<221> NAME/KEY: misc_feature
<222> LOCATION: (3)..(3)
<223> OTHER INFORMATION: 5-(N-tryptaminocarboxyamide)-2'-deoxyuridine
<220> FEATURE:
<221> NAME/KEY: misc_feature
<222> LOCATION: (7)..(7)
<223> OTHER INFORMATION: 5-methyl-2'-deoxycytidine
<220> FEATURE:
<221> NAME/KEY: misc_feature
<222> LOCATION: (9)..(108)
<223> OTHER INFORMATION: any naturally occurring or modified nucleotide;
      may be absent
<220> FEATURE:
<221> NAME/KEY: misc_feature
<222> LOCATION: (112)..(112)
<223> OTHER INFORMATION: 5-(N-tryptaminocarboxyamide)-2'-deoxyuridine
<220> FEATURE:
<221> NAME/KEY: misc_feature
<222> LOCATION: (113)..(113)
<223> OTHER INFORMATION: 5-methyl-2'-deoxycytidine
<220> FEATURE:
<221> NAME/KEY: misc_feature
<222> LOCATION: (114)..(114)
<223> OTHER INFORMATION: 5-(N-tryptaminocarboxyamide)-2'-deoxyuridine
<220> FEATURE:
<221> NAME/KEY: misc_feature
<222> LOCATION: (115)..(117)
<223> OTHER INFORMATION: 5-methyl-2'-deoxycytidine

<400> SEQUENCE: 19
ngnaggnsnn nnnnnnnnnn nnnnnnnnnn nnnnnnnnnn nnnnnnnnnn nnnnnnnnnn    60
nnnnnnnnnn nnnnnnnnnn nnnnnnnnnn nnnnnnnnnn nnnnnnnsg annnnnn       117

<210> SEQ ID NO 20
<211> LENGTH: 57
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 5-methyl-2'-deoxycytidine
<220> FEATURE:
<221> NAME/KEY: misc_feature
<222> LOCATION: (4)..(4)
<223> OTHER INFORMATION: 5-(N-tryptaminocarboxyamide)-2'-deoxyuridine
<220> FEATURE:
<221> NAME/KEY: misc_feature
<222> LOCATION: (5)..(5)
<223> OTHER INFORMATION: 5-methyl-2'-deoxycytidine
<220> FEATURE:
<221> NAME/KEY: misc_feature
<222> LOCATION: (6)..(6)
<223> OTHER INFORMATION: 5-(N-tryptaminocarboxyamide)-2'-deoxyuridine
<220> FEATURE:
<221> NAME/KEY: misc_feature
<222> LOCATION: (10)..(49)
<223> OTHER INFORMATION: any naturally occurring or modified nucleotide;
      may be absent
<220> FEATURE:
<221> NAME/KEY: misc_feature
<222> LOCATION: (51)..(51)
<223> OTHER INFORMATION: 5-methyl-2'-deoxycytidine
<220> FEATURE:
<221> NAME/KEY: misc_feature
<222> LOCATION: (55)..(55)
```

```
<223> OTHER INFORMATION: 5-(N-tryptaminocarboxyamide)-2'-deoxyuridine
<220> FEATURE:
<221> NAME/KEY: misc_feature
<222> LOCATION: (57)..(57)
<223> OTHER INFORMATION: C or a modified nucleotide

<400> SEQUENCE: 20
nnnnnnagsn nnnnnnnnnn nnnnnnnnnn nnnnnnnnnn nnnnnnnns nggangn          57

<210> SEQ ID NO 21
<211> LENGTH: 57
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: C or a modified nucleotide
<220> FEATURE:
<221> NAME/KEY: misc_feature
<222> LOCATION: (3)..(3)
<223> OTHER INFORMATION: 5-(N-tryptaminocarboxyamide)-2'-deoxyuridine
<220> FEATURE:
<221> NAME/KEY: misc_feature
<222> LOCATION: (7)..(7)
<223> OTHER INFORMATION: 5-methyl-2'-deoxycytidine
<220> FEATURE:
<221> NAME/KEY: misc_feature
<222> LOCATION: (9)..(48)
<223> OTHER INFORMATION: any naturally occurring or modified nucleotide;
      may be absent
<220> FEATURE:
<221> NAME/KEY: misc_feature
<222> LOCATION: (52)..(52)
<223> OTHER INFORMATION: 5-(N-tryptaminocarboxyamide)-2'-deoxyuridine
<220> FEATURE:
<221> NAME/KEY: misc_feature
<222> LOCATION: (53)..(53)
<223> OTHER INFORMATION: 5-methyl-2'-deoxycytidine
<220> FEATURE:
<221> NAME/KEY: misc_feature
<222> LOCATION: (54)..(54)
<223> OTHER INFORMATION: 5-(N-tryptaminocarboxyamide)-2'-deoxyuridine
<220> FEATURE:
<221> NAME/KEY: misc_feature
<222> LOCATION: (55)..(55)
<223> OTHER INFORMATION: 5-methyl-2'-deoxycytidine
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (57)..(57)
<223> OTHER INFORMATION: 5-methyl-2'-deoxycytidine

<400> SEQUENCE: 21
ngnaggncnn nnnnnnnnnn nnnnnnnnnn nnnnnnnnnn nnnnnnncg annnnnn          57

<210> SEQ ID NO 22
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5-methyl-2'-deoxycytidine
<220> FEATURE:
<221> NAME/KEY: misc_feature
<222> LOCATION: (4)..(4)
<223> OTHER INFORMATION: 5-methyl-2'-deoxycytidine
<220> FEATURE:
```

-continued

```
<221> NAME/KEY: misc_feature
<222> LOCATION: (9)..(11)
<223> OTHER INFORMATION: 5-methyl-2'-deoxycytidine
<220> FEATURE:
<221> NAME/KEY: misc_feature
<222> LOCATION: (12)..(12)
<223> OTHER INFORMATION: 5-(N-tryptaminocarboxyamide)-2'-deoxyuridine
<220> FEATURE:
<221> NAME/KEY: misc_feature
<222> LOCATION: (13)..(13)
<223> OTHER INFORMATION: 5-methyl-2'-deoxycytidine
<220> FEATURE:
<221> NAME/KEY: misc_feature
<222> LOCATION: (14)..(14)
<223> OTHER INFORMATION: 5-(N-tryptaminocarboxyamide)-2'-deoxyuridine
<220> FEATURE:
<221> NAME/KEY: misc_feature
<222> LOCATION: (17)..(18)
<223> OTHER INFORMATION: 5-methyl-2'-deoxycytidine
<220> FEATURE:
<221> NAME/KEY: misc_feature
<222> LOCATION: (20)..(20)
<223> OTHER INFORMATION: 5-(N-tryptaminocarboxyamide)-2'-deoxyuridine
<220> FEATURE:
<221> NAME/KEY: misc_feature
<222> LOCATION: (22)..(22)
<223> OTHER INFORMATION: 5-methyl-2'-deoxycytidine
<220> FEATURE:
<221> NAME/KEY: misc_feature
<222> LOCATION: (23)..(23)
<223> OTHER INFORMATION: 5-(N-tryptaminocarboxyamide)-2'-deoxyuridine
<220> FEATURE:
<221> NAME/KEY: misc_feature
<222> LOCATION: (24)..(24)
<223> OTHER INFORMATION: 5-methyl-2'-deoxycytidine
<220> FEATURE:
<221> NAME/KEY: misc_feature
<222> LOCATION: (25)..(25)
<223> OTHER INFORMATION: 5-(N-tryptaminocarboxyamide)-2'-deoxyuridine
<220> FEATURE:
<221> NAME/KEY: misc_feature
<222> LOCATION: (27)..(27)
<223> OTHER INFORMATION: 5-(N-tryptaminocarboxyamide)-2'-deoxyuridine
<220> FEATURE:
<221> NAME/KEY: misc_feature
<222> LOCATION: (30)..(30)
<223> OTHER INFORMATION: 5-(N-tryptaminocarboxyamide)-2'-deoxyuridine
<220> FEATURE:
<221> NAME/KEY: misc_feature
<222> LOCATION: (33)..(33)
<223> OTHER INFORMATION: 5-methyl-2'-deoxycytidine
<220> FEATURE:
<221> NAME/KEY: misc_feature
<222> LOCATION: (37)..(37)
<223> OTHER INFORMATION: 5-(N-tryptaminocarboxyamide)-2'-deoxyuridine
<220> FEATURE:
<221> NAME/KEY: misc_feature
<222> LOCATION: (39)..(39)
<223> OTHER INFORMATION: 5-methyl-2'-deoxycytidine
<220> FEATURE:
<221> NAME/KEY: misc_feature
<222> LOCATION: (40)..(40)
<223> OTHER INFORMATION: 5-(N-tryptaminocarboxyamide)-2'-deoxyuridine

<400> SEQUENCE: 22 ngangggnn nnnnagnngn annnngnaan ggnggangnn                          40

<210> SEQ ID NO 23
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: 5-methyl-2'-deoxycytidine
```

```
<220> FEATURE:
<221> NAME/KEY: misc_feature
<222> LOCATION: (8)..(10)
<223> OTHER INFORMATION: 5-methyl-2'-deoxycytidine
<220> FEATURE:
<221> NAME/KEY: misc_feature
<222> LOCATION: (11)..(11)
<223> OTHER INFORMATION: 5-(N-tryptaminocarboxyamide)-2'-deoxyuridine
<220> FEATURE:
<221> NAME/KEY: misc_feature
<222> LOCATION: (12)..(12)
<223> OTHER INFORMATION: 5-methyl-2'-deoxycytidine
<220> FEATURE:
<221> NAME/KEY: misc_feature
<222> LOCATION: (13)..(13)
<223> OTHER INFORMATION: 5-(N-tryptaminocarboxyamide)-2'-deoxyuridine
<220> FEATURE:
<221> NAME/KEY: misc_feature
<222> LOCATION: (16)..(17)
<223> OTHER INFORMATION: 5-methyl-2'-deoxycytidine
<220> FEATURE:
<221> NAME/KEY: misc_feature
<222> LOCATION: (19)..(19)
<223> OTHER INFORMATION: 5-(N-tryptaminocarboxyamide)-2'-deoxyuridine
<220> FEATURE:
<221> NAME/KEY: misc_feature
<222> LOCATION: (21)..(21)
<223> OTHER INFORMATION: 5-methyl-2'-deoxycytidine
<220> FEATURE:
<221> NAME/KEY: misc_feature
<222> LOCATION: (22)..(22)
<223> OTHER INFORMATION: 5-(N-tryptaminocarboxyamide)-2'-deoxyuridine
<220> FEATURE:
<221> NAME/KEY: misc_feature
<222> LOCATION: (23)..(23)
<223> OTHER INFORMATION: 5-methyl-2'-deoxycytidine
<220> FEATURE:
<221> NAME/KEY: misc_feature
<222> LOCATION: (24)..(24)
<223> OTHER INFORMATION: 5-(N-tryptaminocarboxyamide)-2'-deoxyuridine
<220> FEATURE:
<221> NAME/KEY: misc_feature
<222> LOCATION: (26)..(26)
<223> OTHER INFORMATION: 5-(N-tryptaminocarboxyamide)-2'-deoxyuridine
<220> FEATURE:
<221> NAME/KEY: misc_feature
<222> LOCATION: (29)..(29)
<223> OTHER INFORMATION: 5-(N-tryptaminocarboxyamide)-2'-deoxyuridine
<220> FEATURE:
<221> NAME/KEY: misc_feature
<222> LOCATION: (32)..(32)
<223> OTHER INFORMATION: 5-methyl-2'-deoxycytidine
<220> FEATURE:
<221> NAME/KEY: misc_feature
<222> LOCATION: (36)..(36)
<223> OTHER INFORMATION: 5-(N-tryptaminocarboxyamide)-2'-deoxyuridine
<220> FEATURE:
<221> NAME/KEY: misc_feature
<222> LOCATION: (38)..(38)
<223> OTHER INFORMATION: 5-methyl-2'-deoxycytidine
<220> FEATURE:
<221> NAME/KEY: misc_feature
<222> LOCATION: (39)..(39)
<223> OTHER INFORMATION: 5-(N-tryptaminocarboxyamide)-2'-deoxyuridine

<400> SEQUENCE: 23
gangggghnn nnnagnngna nnnngnaang gnggangnn                    39

<210> SEQ ID NO 24
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
```

```
<223> OTHER INFORMATION: 5-methyl-2'-deoxycytidine
<220> FEATURE:
<221> NAME/KEY: misc_feature
<222> LOCATION: (4)..(6)
<223> OTHER INFORMATION: 5-(N-tryptaminocarboxyamide)-2'-deoxyuridine
<220> FEATURE:
<221> NAME/KEY: misc_feature
<222> LOCATION: (8)..(10)
<223> OTHER INFORMATION: 5-methyl-2'-deoxycytidine
<220> FEATURE:
<221> NAME/KEY: misc_feature
<222> LOCATION: (11)..(11)
<223> OTHER INFORMATION: 5-(N-tryptaminocarboxyamide)-2'-deoxyuridine
<220> FEATURE:
<221> NAME/KEY: misc_feature
<222> LOCATION: (12)..(12)
<223> OTHER INFORMATION: 5-methyl-2'-deoxycytidine
<220> FEATURE:
<221> NAME/KEY: misc_feature
<222> LOCATION: (13)..(13)
<223> OTHER INFORMATION: 5-(N-tryptaminocarboxyamide)-2'-deoxyuridine
<220> FEATURE:
<221> NAME/KEY: misc_feature
<222> LOCATION: (16)..(16)
<223> OTHER INFORMATION: 5-methyl-2'-deoxycytidine
<220> FEATURE:
<221> NAME/KEY: misc_feature
<222> LOCATION: (18)..(20)
<223> OTHER INFORMATION: 5-methyl-2'-deoxycytidine
<220> FEATURE:
<221> NAME/KEY: misc_feature
<222> LOCATION: (22)..(22)
<223> OTHER INFORMATION: 5-(N-tryptaminocarboxyamide)-2'-deoxyuridine
<220> FEATURE:
<221> NAME/KEY: misc_feature
<222> LOCATION: (24)..(25)
<223> OTHER INFORMATION: 5-(N-tryptaminocarboxyamide)-2'-deoxyuridine
<220> FEATURE:
<221> NAME/KEY: misc_feature
<222> LOCATION: (27)..(27)
<223> OTHER INFORMATION: 5-methyl-2'-deoxycytidine
<220> FEATURE:
<221> NAME/KEY: misc_feature
<222> LOCATION: (29)..(29)
<223> OTHER INFORMATION: 5-methyl-2'-deoxycytidine
<220> FEATURE:
<221> NAME/KEY: misc_feature
<222> LOCATION: (33)..(33)
<223> OTHER INFORMATION: 5-(N-tryptaminocarboxyamide)-2'-deoxyuridine
<220> FEATURE:
<221> NAME/KEY: misc_feature
<222> LOCATION: (35)..(35)
<223> OTHER INFORMATION: 5-methyl-2'-deoxycytidine
<220> FEATURE:
<221> NAME/KEY: misc_feature
<222> LOCATION: (36)..(36)
<223> OTHER INFORMATION: 5-(N-tryptaminocarboxyamide)-2'-deoxyuridine
<220> FEATURE:
<221> NAME/KEY: misc_feature
<222> LOCATION: (38)..(38)
<223> OTHER INFORMATION: 5-(N-tryptaminocarboxyamide)-2'-deoxyuridine
<220> FEATURE:
<221> NAME/KEY: misc_feature
<222> LOCATION: (40)..(40)
<223> OTHER INFORMATION: 5-(N-tryptaminocarboxyamide)-2'-deoxyuridine

<400> SEQUENCE: 24
ggnnnngnnn nnnagngnnn gnanngngng gangnnangn                            40

<210> SEQ ID NO 25
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

<222> LOCATION: (1)..(4)
<223> OTHER INFORMATION: 5-methyl-2'-deoxycytidine
<220> FEATURE:
<221> NAME/KEY: misc_feature
<222> LOCATION: (6)..(8)
<223> OTHER INFORMATION: 5-methyl-2'-deoxycytidine
<220> FEATURE:
<221> NAME/KEY: misc_feature
<222> LOCATION: (9)..(9)
<223> OTHER INFORMATION: 5-(N-tryptaminocarboxyamide)-2'-deoxyuridine
<220> FEATURE:
<221> NAME/KEY: misc_feature
<222> LOCATION: (10)..(10)
<223> OTHER INFORMATION: 5-methyl-2'-deoxycytidine
<220> FEATURE:
<221> NAME/KEY: misc_feature
<222> LOCATION: (11)..(11)
<223> OTHER INFORMATION: 5-(N-tryptaminocarboxyamide)-2'-deoxyuridine
<220> FEATURE:
<221> NAME/KEY: misc_feature
<222> LOCATION: (14)..(14)
<223> OTHER INFORMATION: 5-methyl-2'-deoxycytidine
<220> FEATURE:
<221> NAME/KEY: misc_feature
<222> LOCATION: (15)..(16)
<223> OTHER INFORMATION: 5-(N-tryptaminocarboxyamide)-2'-deoxyuridine
<220> FEATURE:
<221> NAME/KEY: misc_feature
<222> LOCATION: (18)..(18)
<223> OTHER INFORMATION: 5-methyl-2'-deoxycytidine
<220> FEATURE:
<221> NAME/KEY: misc_feature
<222> LOCATION: (22)..(22)
<223> OTHER INFORMATION: 5-(N-tryptaminocarboxyamide)-2'-deoxyuridine
<220> FEATURE:
<221> NAME/KEY: misc_feature
<222> LOCATION: (24)..(24)
<223> OTHER INFORMATION: 5-methyl-2'-deoxycytidine
<220> FEATURE:
<221> NAME/KEY: misc_feature
<222> LOCATION: (29)..(29)
<223> OTHER INFORMATION: 5-(N-tryptaminocarboxyamide)-2'-deoxyuridine
<220> FEATURE:
<221> NAME/KEY: misc_feature
<222> LOCATION: (32)..(32)
<223> OTHER INFORMATION: 5-methyl-2'-deoxycytidine
<220> FEATURE:
<221> NAME/KEY: misc_feature
<222> LOCATION: (37)..(37)
<223> OTHER INFORMATION: 5-methyl-2'-deoxycytidine
<220> FEATURE:
<221> NAME/KEY: misc_feature
<222> LOCATION: (39)..(39)
<223> OTHER INFORMATION: 5-methyl-2'-deoxycytidine

<400> SEQUENCE: 25
nnnngnnnnn nagnnngngg angngggggng angagangng                40

<210> SEQ ID NO 26
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5-methyl-2'-deoxycytidine
<220> FEATURE:
<221> NAME/KEY: misc_feature
<222> LOCATION: (2)..(2)
<223> OTHER INFORMATION: 5-(N-tryptaminocarboxyamide)-2'-deoxyuridine
<220> FEATURE:
<221> NAME/KEY: misc_feature
<222> LOCATION: (5)..(5)
<223> OTHER INFORMATION: 5-(N-tryptaminocarboxyamide)-2'-deoxyuridine
<220> FEATURE:

```
<221> NAME/KEY: misc_feature
<222> LOCATION: (7)..(9)
<223> OTHER INFORMATION: 5-methyl-2'-deoxycytidine
<220> FEATURE:
<221> NAME/KEY: misc_feature
<222> LOCATION: (10)..(10)
<223> OTHER INFORMATION: 5-(N-tryptaminocarboxyamide)-2'-deoxyuridine
<220> FEATURE:
<221> NAME/KEY: misc_feature
<222> LOCATION: (11)..(11)
<223> OTHER INFORMATION: 5-methyl-2'-deoxycytidine
<220> FEATURE:
<221> NAME/KEY: misc_feature
<222> LOCATION: (12)..(12)
<223> OTHER INFORMATION: 5-(N-tryptaminocarboxyamide)-2'-deoxyuridine
<220> FEATURE:
<221> NAME/KEY: misc_feature
<222> LOCATION: (15)..(15)
<223> OTHER INFORMATION: 5-methyl-2'-deoxycytidine
<220> FEATURE:
<221> NAME/KEY: misc_feature
<222> LOCATION: (16)..(16)
<223> OTHER INFORMATION: 5-(N-tryptaminocarboxyamide)-2'-deoxyuridine
<220> FEATURE:
<221> NAME/KEY: misc_feature
<222> LOCATION: (20)..(20)
<223> OTHER INFORMATION: 5-(N-tryptaminocarboxyamide)-2'-deoxyuridine
<220> FEATURE:
<221> NAME/KEY: misc_feature
<222> LOCATION: (23)..(24)
<223> OTHER INFORMATION: 5-methyl-2'-deoxycytidine
<220> FEATURE:
<221> NAME/KEY: misc_feature
<222> LOCATION: (25)..(25)
<223> OTHER INFORMATION: 5-(N-tryptaminocarboxyamide)-2'-deoxyuridine

<400> SEQUENCE: 26
nnggngnnnn nnagnnggan gannngg                                            27

<210> SEQ ID NO 27
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5-methyl-2'-deoxycytidine
<220> FEATURE:
<221> NAME/KEY: misc_feature
<222> LOCATION: (2)..(2)
<223> OTHER INFORMATION: 5-(N-tryptaminocarboxyamide)-2'-deoxyuridine
<220> FEATURE:
<221> NAME/KEY: misc_feature
<222> LOCATION: (4)..(4)
<223> OTHER INFORMATION: 5-(N-tryptaminocarboxyamide)-2'-deoxyuridine
<220> FEATURE:
<221> NAME/KEY: misc_feature
<222> LOCATION: (6)..(8)
<223> OTHER INFORMATION: 5-methyl-2'-deoxycytidine
<220> FEATURE:
<221> NAME/KEY: misc_feature
<222> LOCATION: (9)..(9)
<223> OTHER INFORMATION: 5-(N-tryptaminocarboxyamide)-2'-deoxyuridine
<220> FEATURE:
<221> NAME/KEY: misc_feature
<222> LOCATION: (10)..(10)
<223> OTHER INFORMATION: 5-methyl-2'-deoxycytidine
<220> FEATURE:
<221> NAME/KEY: misc_feature
<222> LOCATION: (11)..(11)
<223> OTHER INFORMATION: 5-(N-tryptaminocarboxyamide)-2'-deoxyuridine
<220> FEATURE:
<221> NAME/KEY: misc_feature
<222> LOCATION: (14)..(14)
<223> OTHER INFORMATION: 5-methyl-2'-deoxycytidine
```

```
<220> FEATURE:
<221> NAME/KEY: misc_feature
<222> LOCATION: (16)..(16)
<223> OTHER INFORMATION: 5-(N-tryptaminocarboxyamide)-2'-deoxyuridine
<220> FEATURE:
<221> NAME/KEY: misc_feature
<222> LOCATION: (18)..(18)
<223> OTHER INFORMATION: 5-methyl-2'-deoxycytidine
<220> FEATURE:
<221> NAME/KEY: misc_feature
<222> LOCATION: (19)..(20)
<223> OTHER INFORMATION: 5-(N-tryptaminocarboxyamide)-2'-deoxyuridine
<220> FEATURE:
<221> NAME/KEY: misc_feature
<222> LOCATION: (21)..(21)
<223> OTHER INFORMATION: 5-methyl-2'-deoxycytidine
<220> FEATURE:
<221> NAME/KEY: misc_feature
<222> LOCATION: (24)..(24)
<223> OTHER INFORMATION: 5-(N-tryptaminocarboxyamide)-2'-deoxyuridine
<220> FEATURE:
<221> NAME/KEY: misc_feature
<222> LOCATION: (26)..(26)
<223> OTHER INFORMATION: 5-methyl-2'-deoxycytidine
<220> FEATURE:
<221> NAME/KEY: misc_feature
<222> LOCATION: (30)..(30)
<223> OTHER INFORMATION: 5-(N-tryptaminocarboxyamide)-2'-deoxyuridine
<220> FEATURE:
<221> NAME/KEY: misc_feature
<222> LOCATION: (32)..(32)
<223> OTHER INFORMATION: 5-(N-tryptaminocarboxyamide)-2'-deoxyuridine
<220> FEATURE:
<221> NAME/KEY: misc_feature
<222> LOCATION: (34)..(34)
<223> OTHER INFORMATION: 5-(N-tryptaminocarboxyamide)-2'-deoxyuridine
<220> FEATURE:
<221> NAME/KEY: misc_feature
<222> LOCATION: (36)..(38)
<223> OTHER INFORMATION: 5-methyl-2'-deoxycytidine

<400> SEQUENCE: 27
nngnannnnn nagnanannn ngangnggan gnanannngg                    40

<210> SEQ ID NO 28
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 5-methyl-2'-deoxycytidine
<220> FEATURE:
<221> NAME/KEY: misc_feature
<222> LOCATION: (6)..(7)
<223> OTHER INFORMATION: 5-(N-tryptaminocarboxyamide)-2'-deoxyuridine
<220> FEATURE:
<221> NAME/KEY: misc_feature
<222> LOCATION: (9)..(11)
<223> OTHER INFORMATION: 5-methyl-2'-deoxycytidine
<220> FEATURE:
<221> NAME/KEY: misc_feature
<222> LOCATION: (12)..(12)
<223> OTHER INFORMATION: 5-(N-tryptaminocarboxyamide)-2'-deoxyuridine
<220> FEATURE:
<221> NAME/KEY: misc_feature
<222> LOCATION: (13)..(13)
<223> OTHER INFORMATION: 5-methyl-2'-deoxycytidine
<220> FEATURE:
<221> NAME/KEY: misc_feature
<222> LOCATION: (14)..(14)
<223> OTHER INFORMATION: 5-(N-tryptaminocarboxyamide)-2'-deoxyuridine
<220> FEATURE:
<221> NAME/KEY: misc_feature
<222> LOCATION: (17)..(18)
```

<223> OTHER INFORMATION: 5-methyl-2'-deoxycytidine
<220> FEATURE:
<221> NAME/KEY: misc_feature
<222> LOCATION: (19)..(19)
<223> OTHER INFORMATION: 5-(N-tryptaminocarboxyamide)-2'-deoxyuridine

<400> SEQUENCE: 28
gaagnnnann nnnnagnnna                                               20

<210> SEQ ID NO 29
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 5-methyl-2'-deoxycytidine
<220> FEATURE:
<221> NAME/KEY: misc_feature
<222> LOCATION: (4)..(4)
<223> OTHER INFORMATION: 5-methyl-2'-deoxycytidine
<220> FEATURE:
<221> NAME/KEY: misc_feature
<222> LOCATION: (8)..(8)
<223> OTHER INFORMATION: 5-(N-tryptaminocarboxyamide)-2'-deoxyuridine
<220> FEATURE:
<221> NAME/KEY: misc_feature
<222> LOCATION: (9)..(9)
<223> OTHER INFORMATION: 5-methyl-2'-deoxycytidine
<220> FEATURE:
<221> NAME/KEY: misc_feature
<222> LOCATION: (11)..(11)
<223> OTHER INFORMATION: 5-methyl-2'-deoxycytidine
<220> FEATURE:
<221> NAME/KEY: misc_feature
<222> LOCATION: (12)..(12)
<223> OTHER INFORMATION: 5-(N-tryptaminocarboxyamide)-2'-deoxyuridine
<220> FEATURE:
<221> NAME/KEY: misc_feature
<222> LOCATION: (13)..(15)
<223> OTHER INFORMATION: 5-methyl-2'-deoxycytidine
<220> FEATURE:
<221> NAME/KEY: misc_feature
<222> LOCATION: (16)..(16)
<223> OTHER INFORMATION: 5-(N-tryptaminocarboxyamide)-2'-deoxyuridine
<220> FEATURE:
<221> NAME/KEY: misc_feature
<222> LOCATION: (17)..(17)
<223> OTHER INFORMATION: 5-methyl-2'-deoxycytidine
<220> FEATURE:
<221> NAME/KEY: misc_feature
<222> LOCATION: (18)..(18)
<223> OTHER INFORMATION: 5-(N-tryptaminocarboxyamide)-2'-deoxyuridine
<220> FEATURE:
<221> NAME/KEY: misc_feature
<222> LOCATION: (24)..(24)
<223> OTHER INFORMATION: 5-methyl-2'-deoxycytidine
<220> FEATURE:
<221> NAME/KEY: misc_feature
<222> LOCATION: (26)..(26)
<223> OTHER INFORMATION: 5-methyl-2'-deoxycytidine
<220> FEATURE:
<221> NAME/KEY: misc_feature
<222> LOCATION: (28)..(28)
<223> OTHER INFORMATION: 5-methyl-2'-deoxycytidine
<220> FEATURE:
<221> NAME/KEY: misc_feature
<222> LOCATION: (29)..(29)
<223> OTHER INFORMATION: 5-(N-tryptaminocarboxyamide)-2'-deoxyuridine
<220> FEATURE:
<221> NAME/KEY: misc_feature
<222> LOCATION: (32)..(33)
<223> OTHER INFORMATION: 5-methyl-2'-deoxycytidine

<400> SEQUENCE: 29
gngngagnng nnnnnnnnag gaanangnng anng                                    34

<210> SEQ ID NO 30
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: 5-methyl-2'-deoxycytidine
<220> FEATURE:
<221> NAME/KEY: misc_feature
<222> LOCATION: (4)..(5)
<223> OTHER INFORMATION: 5-(N-tryptaminocarboxyamide)-2'-deoxyuridine
<220> FEATURE:
<221> NAME/KEY: misc_feature
<222> LOCATION: (6)..(6)
<223> OTHER INFORMATION: 5-methyl-2'-deoxycytidine
<220> FEATURE:
<221> NAME/KEY: misc_feature
<222> LOCATION: (7)..(7)
<223> OTHER INFORMATION: 5-(N-tryptaminocarboxyamide)-2'-deoxyuridine
<220> FEATURE:
<221> NAME/KEY: misc_feature
<222> LOCATION: (9)..(9)
<223> OTHER INFORMATION: 5-(N-tryptaminocarboxyamide)-2'-deoxyuridine
<220> FEATURE:
<221> NAME/KEY: misc_feature
<222> LOCATION: (10)..(10)
<223> OTHER INFORMATION: 5-methyl-2'-deoxycytidine
<220> FEATURE:
<221> NAME/KEY: misc_feature
<222> LOCATION: (11)..(11)
<223> OTHER INFORMATION: 5-(N-tryptaminocarboxyamide)-2'-deoxyuridine
<220> FEATURE:
<221> NAME/KEY: misc_feature
<222> LOCATION: (13)..(13)
<223> OTHER INFORMATION: 5-(N-tryptaminocarboxyamide)-2'-deoxyuridine
<220> FEATURE:
<221> NAME/KEY: misc_feature
<222> LOCATION: (15)..(15)
<223> OTHER INFORMATION: 5-(N-tryptaminocarboxyamide)-2'-deoxyuridine
<220> FEATURE:
<221> NAME/KEY: misc_feature
<222> LOCATION: (18)..(18)
<223> OTHER INFORMATION: 5-(N-tryptaminocarboxyamide)-2'-deoxyuridine
<220> FEATURE:
<221> NAME/KEY: misc_feature
<222> LOCATION: (21)..(23)
<223> OTHER INFORMATION: 5-methyl-2'-deoxycytidine
<220> FEATURE:
<221> NAME/KEY: misc_feature
<222> LOCATION: (24)..(24)
<223> OTHER INFORMATION: 5-(N-tryptaminocarboxyamide)-2'-deoxyuridine
<220> FEATURE:
<221> NAME/KEY: misc_feature
<222> LOCATION: (25)..(25)
<223> OTHER INFORMATION: 5-methyl-2'-deoxycytidine
<220> FEATURE:
<221> NAME/KEY: misc_feature
<222> LOCATION: (26)..(26)
<223> OTHER INFORMATION: 5-(N-tryptaminocarboxyamide)-2'-deoxyuridine
<220> FEATURE:
<221> NAME/KEY: misc_feature
<222> LOCATION: (31)..(31)
<223> OTHER INFORMATION: 5-(N-tryptaminocarboxyamide)-2'-deoxyuridine
<220> FEATURE:
<221> NAME/KEY: misc_feature
<222> LOCATION: (32)..(32)
<223> OTHER INFORMATION: 5-methyl-2'-deoxycytidine
<220> FEATURE:
<221> NAME/KEY: misc_feature
<222> LOCATION: (33)..(33)
<223> OTHER INFORMATION: 5-(N-tryptaminocarboxyamide)-2'-deoxyuridine

```
<400> SEQUENCE: 30
annnnnnann nangnagngg nnnnnnaggg nnng                                        34

<210> SEQ ID NO 31
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 5-(N-tryptaminocarboxyamide)-2'-deoxyuridine
<220> FEATURE:
<221> NAME/KEY: misc_feature
<222> LOCATION: (5)..(5)
<223> OTHER INFORMATION: 5-(N-tryptaminocarboxyamide)-2'-deoxyuridine
<220> FEATURE:
<221> NAME/KEY: misc_feature
<222> LOCATION: (6)..(6)
<223> OTHER INFORMATION: 5-methyl-2'-deoxycytidine
<220> FEATURE:
<221> NAME/KEY: misc_feature
<222> LOCATION: (9)..(9)
<223> OTHER INFORMATION: 5-(N-tryptaminocarboxyamide)-2'-deoxyuridine
<220> FEATURE:
<221> NAME/KEY: misc_feature
<222> LOCATION: (14)..(14)
<223> OTHER INFORMATION: 5-(N-tryptaminocarboxyamide)-2'-deoxyuridine
<220> FEATURE:
<221> NAME/KEY: misc_feature
<222> LOCATION: (16)..(16)
<223> OTHER INFORMATION: 5-methyl-2'-deoxycytidine
<220> FEATURE:
<221> NAME/KEY: misc_feature
<222> LOCATION: (19)..(19)
<223> OTHER INFORMATION: 5-(N-tryptaminocarboxyamide)-2'-deoxyuridine
<220> FEATURE:
<221> NAME/KEY: misc_feature
<222> LOCATION: (22)..(22)
<223> OTHER INFORMATION: 5-methyl-2'-deoxycytidine
<220> FEATURE:
<221> NAME/KEY: misc_feature
<222> LOCATION: (24)..(24)
<223> OTHER INFORMATION: 5-methyl-2'-deoxycytidine
<220> FEATURE:
<221> NAME/KEY: misc_feature
<222> LOCATION: (26)..(28)
<223> OTHER INFORMATION: 5-methyl-2'-deoxycytidine
<220> FEATURE:
<221> NAME/KEY: misc_feature
<222> LOCATION: (29)..(29)
<223> OTHER INFORMATION: 5-(N-tryptaminocarboxyamide)-2'-deoxyuridine
<220> FEATURE:
<221> NAME/KEY: misc_feature
<222> LOCATION: (30)..(30)
<223> OTHER INFORMATION: 5-methyl-2'-deoxycytidine
<220> FEATURE:
<221> NAME/KEY: misc_feature
<222> LOCATION: (31)..(31)
<223> OTHER INFORMATION: 5-(N-tryptaminocarboxyamide)-2'-deoxyuridine

<400> SEQUENCE: 31
anggnngana ggananaaang anangnnnnn nagg                                        34

<210> SEQ ID NO 32
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5-methyl-2'-deoxycytidine
```

```
-continued

<220> FEATURE:
<221> NAME/KEY: misc_feature
<222> LOCATION: (2)..(2)
<223> OTHER INFORMATION: 5-(N-tryptaminocarboxyamide)-2'-deoxyuridine
<220> FEATURE:
<221> NAME/KEY: misc_feature
<222> LOCATION: (4)..(4)
<223> OTHER INFORMATION: 5-methyl-2'-deoxycytidine
<220> FEATURE:
<221> NAME/KEY: misc_feature
<222> LOCATION: (8)..(8)
<223> OTHER INFORMATION: 5-(N-tryptaminocarboxyamide)-2'-deoxyuridine
<220> FEATURE:
<221> NAME/KEY: misc_feature
<222> LOCATION: (10)..(10)
<223> OTHER INFORMATION: 5-methyl-2'-deoxycytidine
<220> FEATURE:
<221> NAME/KEY: misc_feature
<222> LOCATION: (13)..(13)
<223> OTHER INFORMATION: 5-(N-tryptaminocarboxyamide)-2'-deoxyuridine

<400> SEQUENCE: 32
nngnggangn gan                                                              13

<210> SEQ ID NO 33
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 5-methyl-2'-deoxycytidine
<220> FEATURE:
<221> NAME/KEY: misc_feature
<222> LOCATION: (3)..(5)
<223> OTHER INFORMATION: 5-(N-tryptaminocarboxyamide)-2'-deoxyuridine
<220> FEATURE:
<221> NAME/KEY: misc_feature
<222> LOCATION: (9)..(9)
<223> OTHER INFORMATION: 5-methyl-2'-deoxycytidine
<220> FEATURE:
<221> NAME/KEY: misc_feature
<222> LOCATION: (13)..(13)
<223> OTHER INFORMATION: 5-(N-tryptaminocarboxyamide)-2'-deoxyuridine
<220> FEATURE:
<221> NAME/KEY: misc_feature
<222> LOCATION: (15)..(16)
<223> OTHER INFORMATION: 5-(N-tryptaminocarboxyamide)-2'-deoxyuridine

<400> SEQUENCE: 33
gnnnnaggng gangnngaaa                                                       20
```

APTAMERS TO 4-1BB AND THEIR USE IN TREATING DISEASES AND DISORDERS

RELATED APPLICATIONS

This application is a divisional application of Ser. No. 13/582,332, filed Aug. 31, 2012, which is a 35 U.S.C. §371 national phase application of PCT/US2011/027064, filed Mar. 3, 2011 (WO 2011/109642), entitled "Aptamers to 4-1BB and Their Use in Treating Diseases and Disorders," all of which are incorporated herein by reference in their entirety.

FIELD OF THE INVENTION

The present disclosure relates generally to the field of nucleic acids and more particularly to aptamers capable of binding to 4-1BB(CD137), pharmaceutical compositions comprising such 4-1BB aptamers, and methods of making the same. The disclosure further relates to materials and methods for the administration of aptamers capable of binding to 4-1BB.

Incorporated by reference herein in its entirety is the Sequence Listing entitled "sequence Listing.txt", created Mar. 3, 2011, size of 18 kilobytes.

BACKGROUND

The following description provides a summary of information relevant to the present disclosure and is not an admission that any of the information provided or publications referenced herein is prior art to the present disclosure.

The innate immune system of humans and animals is known to have an anti-cancer response. Some tumor cells express antigens which are recognized by the immune system such as mutated gene products (P. van der Bruggen et al., Immunological Rev., 188:51-64, 2002). Treatments such as adoptive immunotherapy or immunomodulators such as cytokines have resulted in tumor regression (S. Antonia et al., Current Opinion in Immunol., 16:130-136, 2004; S. Rosenberg, Cancer J. Sci. Am., 6(S):2, 2000). However, these types of immunotherapies haven't proven broadly effective at eradicating tumor cells. It is thought that immunosuppressive responses in the microenvironment of the tumor, poor antigen recognition on tumor cells, and a lack of co-stimulatory signaling molecules are responsible for the poor performance. As a result, molecules which generate co-stimulatory responses have become desirable for therapies aimed at enhancing anti-tumor immune response.

T cell activation and response is a complex process that requires both antigen-specific T cell receptor engagement as well as other co-stimulatory signals. These co-stimulatory signals can have different functions such as simply enhancing the initial T cell receptor activation, promoting T cell proliferation, inducing cytokine production, or cytotoxicity. There are many different receptors considered co-stimulatory. The tumor-necrosis factor receptor superfamily is one of two main groups of co-stimulatory receptors and 4-1BB(CD 137) is a member of this superfamily. Proteins in this family are involved in the regulation of cell proliferation, differentiation, and programmed cell death.

4-1BB is a type I membrane glycoprotein that was initially described in mice (B. Kwon et al., P.N.A.S. USA, 86:1963-1967, 1989) and is a 30 kDa type I membrane glycoprotein expressed as 55 kDa homodimer. It has also been identified in humans (M. Alderson et al., Eur. J. Immunol., 24:2219-2227, 1994) and the two forms are 60% identical at the amino acid level. 4-1BB is mainly found on lymphoid originating cells such as Natural Killer (NK), NKT-cells, activated T cells, CD4CD25 regulatory T-cells, activated thymocytes, and intraepithelial lymphocytes. It has also been found on dendritic cells, neutrophils, and eosinophils.

4-1BB is expressed on active CD4+ and CD8+ T-cells, but has a much stronger co-stimulatory effect on CD8+ T-cells in vivo (M. Croft, Nat. Rev. Immunol., 3:609-620, 2003). Both expression of 4-1BB ligand in tumor cells and administration of agonistic 4-1BB antibodies have been demonstrated to provide enhanced tumor immunity in mice (S. Mogi et al. 2000. Immunology, 101:541-547, 2003; E. Kocak et al., Cancer Res., 66:7276-7284, 2006). Altogether, 4-1BB stimulation results in enhanced expansion, survival, and effector functions of newly primed CD8+ T-cells, acting, in part, directly on these cells. Based on the critical role of 4-1BB stimulation in CD8+ T-cell function and survival, manipulation of the 4-1BB/4-1BBL system provides a plausible approach for the treatment of tumors and viral pathogens.

In addition to its role in the development of immunity to cancer, experimental data supports the use of 4-1BB agonistic antibodies for the treatment of autoimmune and viral diseases (B. Kwon et al., Exp. Mol. Med., 35(1):8-16, 2003; H. Salih et al., J. Immunol., 167(7):4059-4066; 2001; E. Kwon et al., P.N.A.S. USA, 96:15074-15079, 1999; J. Foell et al., N.Y. Acad. Sci., 987:230-235, 2003; Y. Sun et al., Nat. Med., 8(12):1405-1413, 2002; S. K. Seo et al., Nat. Med., 10:1099-1094, 2004).

Given the variety of important roles 4-1BB has in effecting immune response, generating molecules which bind this receptor and compete with its cognate ligand 4-1BBL represent an important potential therapeutic approach for a variety of human diseases such as cancer, autoimmune disease, and infectious disease. Given the strong interest in generating antibodies to this target, producing high affinity aptamers to this target is an important alternative. Aptamers can be more easily produced, more reproducibly manufactured, and are significantly cheaper.

SUMMARY

The present disclosure provides aptamers that specifically bind to 4-1BB, especially human 4-1BB (or h4-1BB) that have high affinity for 4-1BB. The aptamers of the present disclosure inhibit the binding of 4-1BB to a 4-1BB receptor ligand (4-1BBL or h4-1BBL). As such, the aptamers of the disclosure have wide therapeutic applications as immunomodulators of diseases such as cancer, autoimmune diseases, inflammatory diseases and infectious diseases. Included are pharmaceutical compositions or formulations comprised of a 4-1BB aptamer or a pharmaceutically acceptable salt thereof.

The disclosure also provides pharmaceutical compositions comprising a 4-1BB aptamer of the disclosure and a pharmaceutically acceptable carrier. The compositions of the present disclosure can be prepared in any suitable pharmaceutically acceptable dosage form. The formulations and dosages described herein are designed to maximize clinical efficacy, while simultaneously decreasing or minimizing adverse side effects. The pharmaceutical composition can be administered alone or in combination with an agent, e.g., an agent for treating cancer such as a chemotherapeutic agent or other immunomodulatory agent.

The present disclosure further provides methods for preventing, treating or ameliorating diseases such as cancer, autoimmune diseases, inflammatory diseases, and infectious diseases, the methods comprising administering a 4-1BB aptamer or a pharmaceutical composition of the 4-1BB aptamer to a vertebrate, specifically a mammal, more specifically a human.

In one embodiment, a therapeutic effect may be achieved by administering a 4-1BB aptamer such that the aptamer is exposed to, and can bind to, 4-1BB regardless of the method of delivery of the aptamer to the patient being treated. In a related embodiment, the therapeutic effect may be achieved by the administration of the 4-1BB aptamer such that it is exposed to, and binds to, 4-1BB and thereby prevents or reduces the binding of 4-1BB to a 4-1BB receptor ligand (4-1BBL).

In one aspect, the disclosure provides methods for treating cancer in a subject comprising administering a therapeutically effective amount of a 4-1BB aptamer to the subject. The cancer can be for example, prostate cancer, melanoma, or epithelial cancer.

In yet another aspect, the disclosure may provide a method for enhancing the immune response, comprising administration of a 4-1BB aptamer to a patient. In one aspect, the present disclosure may provide aptamers with agonistic activities in that binding of the aptamers to 4-1BB will result in an enhancement and stimulation of 4-1BB mediated immune responses. These aptamers can be used as immuno-enhancers of an anti-tumor or anti-viral immune response, or as immunomodulators of T cell mediated autoimmune diseases.

The provided methods encompass administration of the 4-1BB aptamer in association with one or more secondary active agents. Such administration can be sequential or in a combination composition.

The 4-1BB aptamers described herein can also be used as diagnostic tools. Thus, in another aspect, the present disclosure provides an in vitro diagnostic method for the detection of 4-1BB in blood or tissues of patients with cancer, autoimmune, or other diseases, said method comprising contacting a 4-1BB aptamer with a sample suspected of comprising 4-1BB. In another aspect, the disclosure provides a diagnostic composition for diagnosis of immune dysfunctions related to over- or under-reactivity of 4-1BB receptor protein.

BRIEF DESCRIPTION OF THE DRAWINGS

FIG. 1 illustrates that co-immunoprecipitation of 4-1BB Ligand by 4-1BB receptor is inhibited by SOMAmer 1684-40 (SEQ ID NO: 6) (FIG. 1A) and not a dT substituted control SOMAmer 1684-40_11 (FIG. 1B). The darkest upper band is 4-1BB receptor, and the lowest band is 4-1BB ligand, the other bands on the gel are bead-associated proteins that are dissociated from the beads during sample preparation. Lane identification from left to right; Lane 1: Protein Standard (Invitrogen), Lane 2: Blank, Lane 3: 100 µM SOMAmer, Lane 4: 75 µM SOMAmer, Lane 5: 50 µM SOMAmer, Lane 6: 25 µM SOMAmer, Lane 7: 10 µM SOMAmer, Lane 8: 5 µM SOMAmer, Lane 9: 2.5 µM SOMAmer, Lane 10:1 µM SOMAmer, Lane 11: 0.5 µM SOMAmer, Lane 12: 0.3 µM SOMAmer, Lane 13: No SOMAmer Control, Lane 14: No Ligand Control.

FIG. 2 depicts a graphical representation of band intensity converted to % inhibition of 4-1BB receptor capture of 4-1BB ligand by SOMAmer 1684-40 (SEQ ID NO: 6) and a dT substituted negative control oligonucleotide 1684-40_11. The $IC_{50}$ of 1684-40 (SEQ ID NO: 6) is $8.1 \times 10^{-10}$ M.

FIG. 8 depicts active full length sequences identified, including affinity-active clones 1684-40 (SEQ ID NO: 6) and 1684-44 (SEQ ID NO: 7).

FIG. 9A depicts aptamer consensus sequences identified containing the two noncontiguous consensus sequence strings (A and B). This figure depicts primarily the random region of the sequences of FIG. 8. The sequences are shown 5' to 3', wherein X=G or C; Y=G or C; Z=C or T; wherein T=TrpdU and C=MdC; wherein M=5'-methyl. Lower case letters represent the fixed region sequences. FIG. 9B depicts the consensus model for the aptamers depicted in FIG. 9A. The consensus was comprised of 2 noncontiguous sequence strings (A and B) of lengths 9 and 8, respectively separated by non-conserved linker sequence (L1 (linker 1) or L2 (linker 2)) of variable length. As depicted in FIG. 9B the A and B portions of consensus may be circularly permuted as shown in 1) and 2). 5f=5'-flanking region; 3f=3'-flanking region. Linkers L1 and 2 and flanking regions 5f and 3f have a length independently selected from n=0 to 100 and are comprised of nucleotides, spacer sequences or a combination thereof.

FIG. 10 depicts an aptamer consensus frequency table for aptamer consensus sequence A and aptamer consensus sequence B.

DETAILED DESCRIPTION

Figure 3:
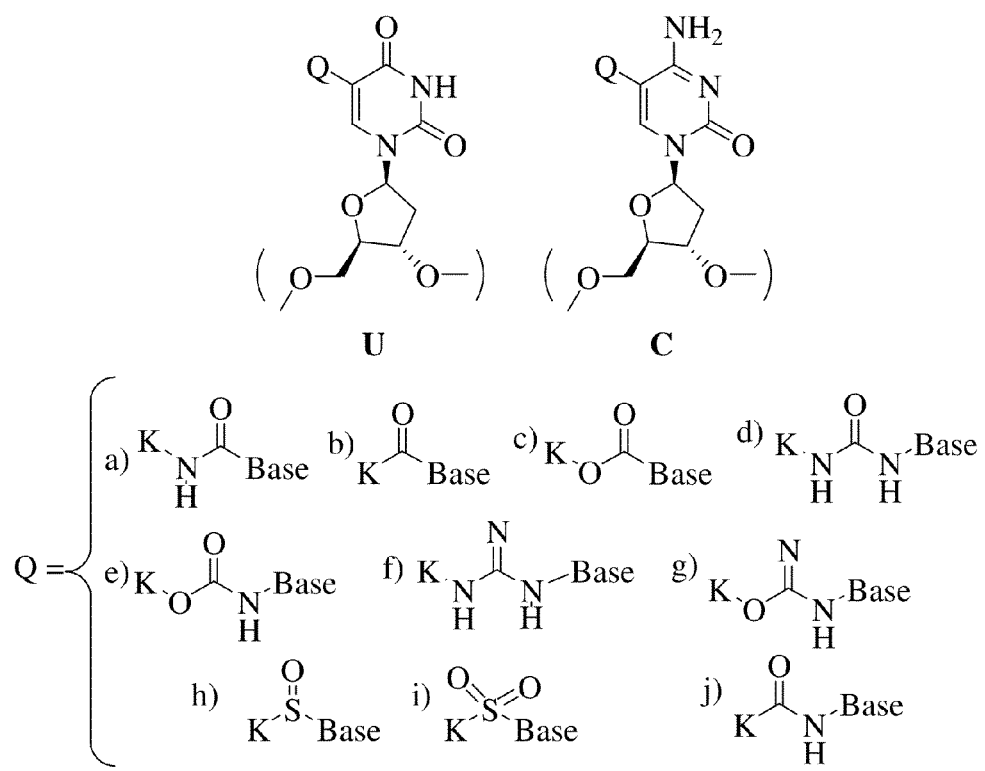
FIG. 3 depicts representative C-5 pyrimidine modifications of the instant disclosure.
Figure 3:
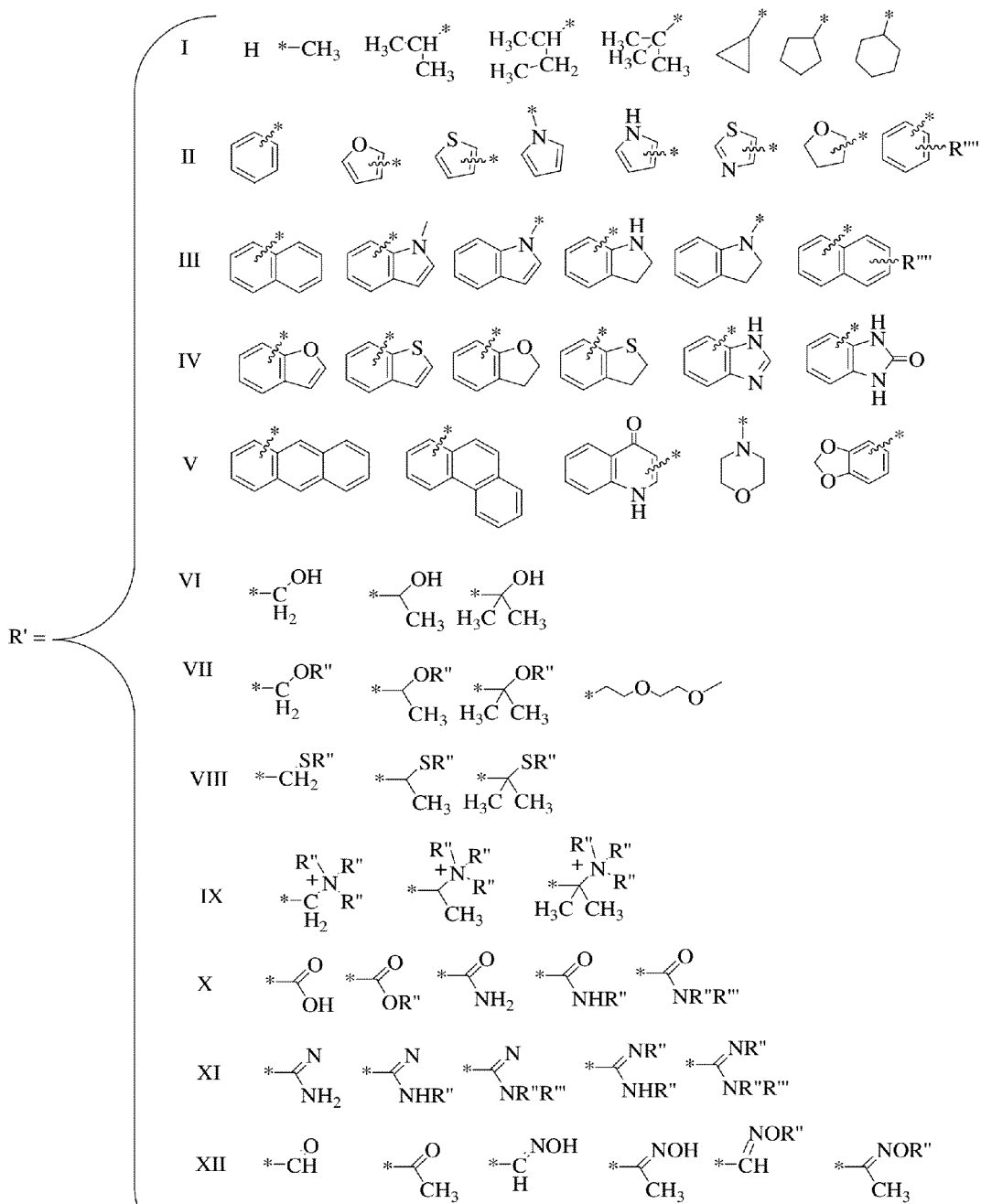
Figure 4:
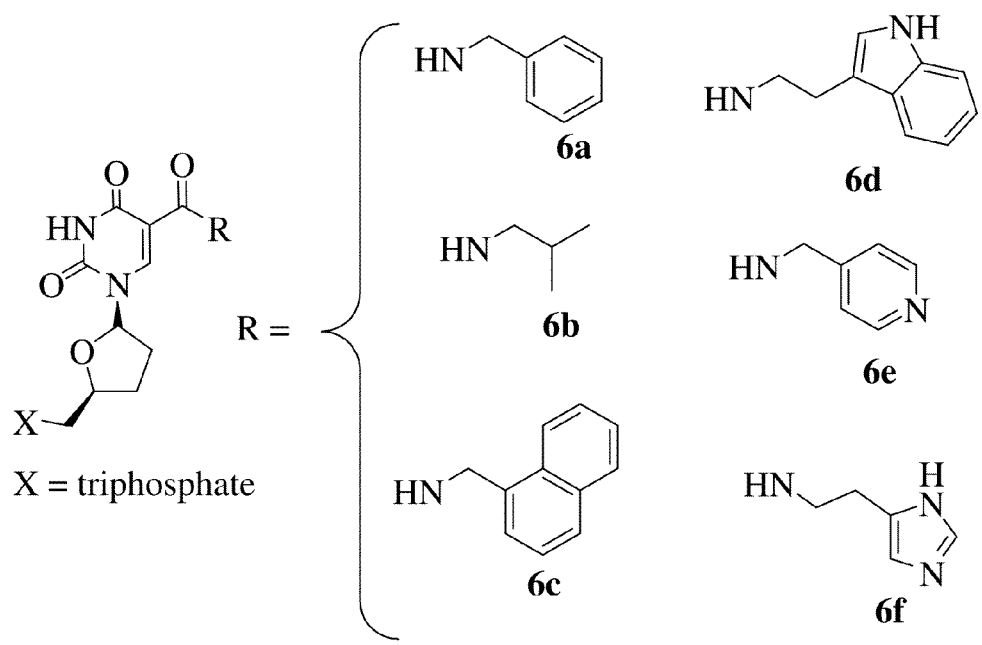
FIG. 4 depicts C-5 pyrimidine modifications 6a-6f.

Reference will now be made in detail to representative embodiments of the invention. While the invention will be described in conjunction with the enumerated embodiments, it will be understood that the invention is not intended to be limited to those embodiments. On the contrary, the invention is intended to cover all alternatives, modifications, and equivalents that may be included within the scope of the present invention as defined by the claims.

One skilled in the art will recognize many methods and materials similar or equivalent to those described herein, which could be used in and are within the scope of the practice of the present disclosure. The present disclosure is in no way limited to the methods and materials described.

Unless defined otherwise, technical and scientific terms used herein have the same meaning as commonly understood by one of ordinary skill in the art(s) to which this invention belongs. Although any methods, devices, and materials similar or equivalent to those described herein can be used in the practice or testing of the invention, the preferred methods, devices and materials are now described.

All publications, published patent documents, and patent applications cited in this disclosure are indicative of the level of skill in the art(s) to which the disclosure pertains. All publications, published patent documents, and patent applications cited herein are hereby incorporated by reference to the same extent as though each individual publication, published patent document, or patent application was specifically and individually indicated as being incorporated by reference.

As used in this disclosure, including the appended claims, the singular forms "a," "an," and "the" include plural references, unless the content clearly dictates otherwise, and are used interchangeably with "at least one" and "one or more." Thus, reference to "an aptamer" includes mixtures of aptamers, and the like.

As used herein, the term "about" represents an insignificant modification or variation of the numerical value such that the basic function of the item to which the numerical value relates is unchanged.

The term "each" when used herein to refer to a plurality of items is intended to refer to at least two of the items. It need not require that all of the items forming the plurality satisfy an associated additional limitation.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

As used herein, the term "nucleotide" refers to a ribonucleotide or a deoxyribonucleotide, or a modified form thereof, as well as an analog thereof. Nucleotides include species that include purines (e.g., adenine, hypoxanthine, guanine, and their derivatives and analogs) as well as pyrimidines (e.g., cytosine, uracil, thymine, and their derivatives and analogs).

As used herein, "nucleic acid," "oligonucleotide," and "polynucleotide" are used interchangeably to refer to a polymer of nucleotides and include DNA, RNA, DNA/RNA hybrids and modifications of these kinds of nucleic acids, oligonucleotides and polynucleotides, wherein the attachment of various entities or moieties to the nucleotide units at any position are included. The terms "polynucleotide," "oligonucleotide," and "nucleic acid" include double- or single-stranded molecules as well as triple-helical molecules. Nucleic acid, oligonucleotide, and polynucleotide are broader terms than the term aptamer and, thus, the terms nucleic acid, oligonucleotide, and polynucleotide include polymers of nucleotides that are aptamers but the terms nucleic acid, oligonucleotide, and polynucleotide are not limited to aptamers.

As used herein, the terms "modify," "modified," "modification," and any variations thereof, when used in reference to an oligonucleotide, means that at least one of the four constituent nucleotide bases (i.e., A, G, T/U, and C) of the oligonucleotide is an analog or ester of a naturally occurring nucleotide. In some embodiments, the modified nucleotide confers nuclease resistance to the oligonucleotide. A pyrimidine with a substitution at the C-5 position is an example of a modified nucleotide. Modifications can include backbone modifications, methylations, unusual base-pairing combinations such as the isobases isocytidine and isoguanidine, and the like. Modifications can also include 3' and 5' modifications, such as capping. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present on the sugar of a nucleotide may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, polyethylene glycol (PEG) polymers in one embodiment ranging from about 10 to about 80 kDa, PEG polymers in another embodiment ranging from about 20 to about 60 kDa, or other hydrophilic or hydrophobic biological or synthetic polymers. In one embodiment, modifications are of the C-5 position of pyrimidines. These modifications can be produced through an amide linkage directly at the C-5 position or by other types of linkages.

Polynucleotides can also contain analogous forms of ribose or deoxyribose sugars that are generally known in the art, including 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. As noted above, one or more phosphodiester linkages may be replaced by alternative linking groups. These alternative linking groups include embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Substitution of analogous forms of sugars, purines, and pyrimidines can be advantageous in designing a final product, as can alternative backbone structures like a polyamide backbone, for example.

As used herein, the term "C-5 modified pyrimidine" refers to a pyrimidine with a modification at the C-5 position including, but not limited to, those moieties illustrated in FIG. 3. Examples of a C-5 modified pyrimidine include those described in U.S. Pat. Nos. 5,719,273 and 5,945,527, as well as, U.S. Provisional Application Ser. No. 61/422,957, filed Dec. 14, 2010, entitled "Nuclease Resistant Oligonucleotides." Specific examples of a C-5 modification include substitution of deoxyuridine at the C-5 position with a substituent independently selected from: benzylcarboxyamide (alternatively benzylaminocarbonyl) (Bn), naphthylmethylcarboxyamide (alternatively naphthylmethylaminocarbonyl) (Nap), tryptaminocarboxyamide (alternatively tryptaminocarbonyl) (Trp), and isobutylcarboxyamide (alternatively isobutylaminocarbonyl) (iBu) as illustrated immediately below.

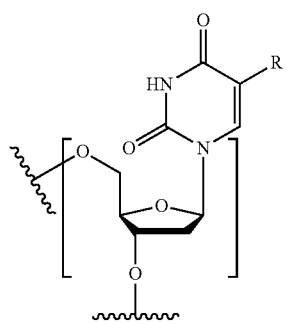

-continued

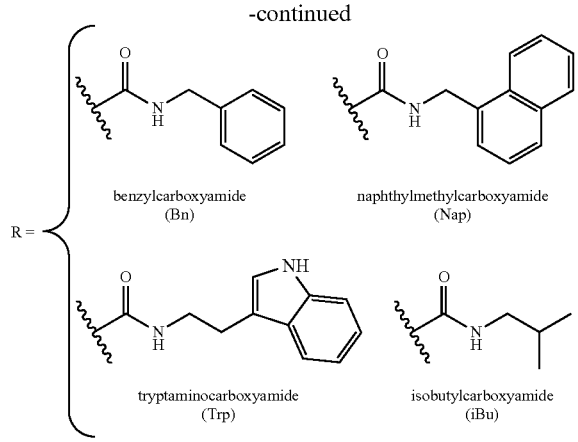

Chemical modifications of a C-5 modified pyrimidine can also be combined with, singly or in any combination, 2'-position sugar modifications, modifications at exocyclic amines, and substitution of 4-thiouridine and the like.

Representative C-5 modified pyrimidines include: 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium)propyl]carboxyamide)-2'-deoxyuridine chloride, 5-(N-naphthylmethylcarboxyamide)-2'-deoxyuridine (NapdU), 5-(N-naphthylmethylcarboxyamide)-2'-O-methyluridine, 5-(N-naphthylmethylcarboxyamide)-2'-fluorouridine or 5-(N-[1-(2,3-dihydroxypropyl)]carboxyamide)-2'-deoxyuridine).

If present, a modification to the nucleotide structure can be imparted before or after assembly of a polymer. A sequence of nucleotides can be interrupted by non-nucleotide components. A polynucleotide can be further modified after polymerization, such as by conjugation with a labeling component.

As used herein, the term "at least one pyrimidine," when referring to modifications of a nucleic acid, refers to one, several, or all pyrimidines in the nucleic acid, indicating that any or all occurrences of any or all of C, T, or U in a nucleic acid may be modified or not.

As used herein, "nucleic acid ligand," "aptamer," and "clone" are used interchangeably to refer to a non-naturally occurring nucleic acid that has a desirable action on a target molecule. A desirable action includes, but is not limited to, binding of the target, catalytically changing the target, reacting with the target in a way that modifies or alters the target or the functional activity of the target, covalently attaching to the target (as in a suicide inhibitor), and facilitating the reaction between the target and another molecule. In one embodiment, the action is specific binding affinity for a target molecule, such target molecule being a three dimensional chemical structure other than a polynucleotide that binds to the nucleic acid ligand through a mechanism which is independent of Watson/Crick base pairing or triple helix formation, wherein the aptamer is not a nucleic acid having the known physiological function of being bound by the target molecule. Aptamers to a given target include nucleic acids that are identified from a candidate mixture of nucleic acids, where the aptamer is a ligand of the target, by a method comprising: (a) contacting the candidate mixture with the target, wherein nucleic acids having an increased affinity to the target relative to other nucleic acids in the candidate mixture can be partitioned from the remainder of the candidate mixture; (b) partitioning the increased affinity nucleic acids from the remainder of the candidate mixture; and (c) amplifying the increased affinity nucleic acids to yield a ligand-enriched mixture of nucleic acids, whereby aptamers of the target molecule are identified. It is recognized that affinity interactions are a matter of degree; however, in this context, the "specific binding affinity" of an aptamer for its target means that the aptamer binds to its target generally with a much higher degree of affinity than it binds to other, non-target, components in a mixture or sample. An "aptamer" or "nucleic acid ligand" is a set of copies of one type or species of nucleic acid molecule that has a particular nucleotide sequence. An aptamer can include any suitable number of nucleotides. "Aptamers" refer to more than one such set of molecules. Different aptamers can have either the same or different numbers of nucleotides. Aptamers may be DNA or RNA and may be single stranded, double stranded, or contain double stranded or triple stranded regions.

As used herein, a "SOMAmer" or Slow Off-Rate Modified Aptamer refers to an aptamer having improved off-rate characteristics. SOMAmers can be generated using the improved SELEX methods described in U.S. Publication No. 20090004667, entitled "Method for Generating Aptamers with Improved Off-Rates.".

As used herein, "protein" is used synonymously with "peptide," "polypeptide," or "peptide fragment." A "purified" polypeptide, protein, peptide, or peptide fragment is substantially free of cellular material or other contaminating proteins from the cell, tissue, or cell-free source from which the amino acid sequence is obtained, or substantially free from chemical precursors or other chemicals when chemically synthesized.

As used herein, "modulate" means to alter, either by increasing or decreasing, the level of a peptide or polypeptide, or to alter, either by increasing or decreasing, the stability or activity of a peptide or a polypeptide. The term "inhibit" means to decrease the level of a peptide or a polypeptide or to decrease the stability or activity of a peptide or a polypeptide. As described herein, the protein which is modulated is 4-1BB.

As used herein, the term "bioactivity" indicates an effect on one or more cellular or extracellular process (e.g., via binding, signaling, etc.) which can impact physiological or pathophysiological processes.

A "4-1BB aptamer" is an aptamer that is capable of binding to and modifying the activity of 4-1BB. In one aspect, a 4-1BB aptamer inhibits the binding of 4-1BB to a 4-1BB receptor ligand (4-1BBL).

As utilized herein, the term "pharmaceutically acceptable" means approved by a regulatory agency of a federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to, such sterile liquids as water and oils.

A "pharmaceutically acceptable salt" or "salt" of a 4-1BB aptamer is a product of the disclosed compound that contains an ionic bond and is typically produced by reacting the disclosed compound with either an acid or a base, suitable for administering to an individual. A pharmaceutically acceptable salt can include, but is not limited to, acid addition salts including hydrochlorides, hydrobromides, phosphates, sulphates, hydrogen sulphates, alkylsulphonates, arylsulphonates, arylalkylsulfonates, acetates, benzoates, citrates, maleates, fumarates, succinates, lactates, and tartrates; alkali metal cations such as Li, Na, K, alkali earth metal salts such as Mg or Ca, or organic amine salts.

A "pharmaceutical composition" is a formulation comprising a 4-1BB aptamer in a form suitable for administration to an individual. A pharmaceutical composition is typically formulated to be compatible with its intended route of administration. Examples of routes of administration include, but are not limited to, oral and parenteral, e.g., intravenous, intradermal, subcutaneous, inhalation, topical, transdermal, transmucosal, and rectal administration.

As used herein, the term "therapeutically effective amount" generally means the amount necessary to ameliorate at least one symptom of a disorder or condition to be prevented, reduced, or treated as described herein. The phrase "therapeutically effective amount" as it relates to the 4-1BB aptamers of the present disclosure means the aptamer dosage that provides the specific pharmacological response for which the aptamer is administered in a significant number of individuals in need of such treatment. It is emphasized that a therapeutically effective amount of an aptamer that is administered to a particular individual in a particular instance will not always be effective in treating the conditions/diseases described herein, even though such dosage is deemed to be a therapeutically effective amount by those of skill in the art.

The SELEX Method

The terms "SELEX" and "SELEX process" are used interchangeably herein to refer generally to a combination of (1) the selection of nucleic acids that interact with a target molecule in a desirable manner, for example binding with high affinity to a protein, with (2) the amplification of those selected nucleic acids. The SELEX process can be used to identify aptamers with high affinity to a specific target molecule or biomarker.

SELEX generally includes preparing a candidate mixture of nucleic acids, binding of the candidate mixture to the desired target molecule to form an affinity complex, separating the affinity complexes from the unbound candidate nucleic acids, separating and isolating the nucleic acid from the affinity complex, purifying the nucleic acid, and identifying a specific aptamer sequence. The process may include multiple rounds to further refine the affinity of the selected aptamer. The process can include amplification steps at one or more points in the process. See, e.g., U.S. Pat. No. 5,475,096, entitled "Nucleic Acid Ligands." The SELEX process can be used to generate an aptamer that covalently binds its target as well as an aptamer that non-covalently binds its target. See, e.g., U.S. Pat. No. 5,705,337 entitled "Systematic Evolution of Nucleic Acid Ligands by Exponential Enrichment: Chemi-SELEX."

The SELEX process can be used to identify high-affinity aptamers containing modified nucleotides that confer improved characteristics on the aptamer, such as, for example, improved in vivo stability or improved delivery characteristics. Examples of such modifications include chemical substitutions at the ribose and/or phosphate and/or base positions. SELEX process-identified aptamers containing modified nucleotides are described in U.S. Pat. No. 5,660,985, entitled "High Affinity Nucleic Acid Ligands Containing Modified Nucleotides," which describes oligonucleotides containing nucleotide derivatives chemically modified at the 5'- and 2'-positions of pyrimidines. U.S. Pat. No. 5,580,737, see supra, describes highly specific aptamers containing one or more nucleotides modified with 2'-amino (2'-$NH_2$), 2'-fluoro (2'-F), and/or 2'-O-methyl (2'-OMe). See also, U.S. Patent Application Publication No. 20090098549, entitled "SELEX and PHOTOSELEX," which describes nucleic acid libraries having expanded physical and chemical properties and their use in SELEX and photoSELEX.

SELEX can also be used to identify aptamers that have desirable off-rate characteristics. See U.S. Patent Publication No. 20090004667, entitled "Method for Generating Aptamers with Improved Off-Rates," which describes improved SELEX methods for generating aptamers that can bind to target molecules. Methods for producing aptamers and photoaptamers having slower rates of dissociation from their respective target molecules are described. The methods involve contacting the candidate mixture with the target molecule, allowing the formation of nucleic acid-target complexes to occur, and performing a slow off-rate enrichment process wherein nucleic acid-target complexes with fast dissociation rates dissociate and do not reform, while complexes with slow dissociation rates remain intact. Additionally, the methods include the use of modified nucleotides in the production of candidate nucleic acid mixtures to generate aptamers with improved off-rate performance (see U.S. Patent Publication No. 20090098549, entitled "SELEX and PhotoSELEX").

"Target" or "target molecule" or "target" refers herein to any compound upon which a nucleic acid can act in a desirable manner. A target molecule can be a protein, peptide, nucleic acid, carbohydrate, lipid, polysaccharide, glycoprotein, hormone, receptor, antigen, antibody, virus, pathogen, toxic substance, substrate, metabolite, transition state analog, cofactor, inhibitor, drug, dye, nutrient, growth factor, cell, tissue, any portion or fragment of any of the foregoing, etc., without limitation. Virtually any chemical or biological effector may be a suitable target. Molecules of any size can serve as targets. A target can also be modified in certain ways to enhance the likelihood or strength of an interaction between the target and the nucleic acid. A target can also include any minor variation of a particular compound or molecule, such as, in the case of a protein, for example, minor variations in amino acid sequence, disulfide bond formation, glycosylation, lipidation, acetylation, phosphorylation, or any other manipulation or modification, such as conjugation with a labeling component, which does not substantially alter the identity of the molecule. A "target molecule" or "target" is a set of copies of one type or species of molecule or multimolecular structure that is capable of binding to an aptamer. "Target molecules" or "targets" refer to more than one such set of molecules. Embodiments of the SELEX process in which the target is a peptide are described in U.S. Pat. No. 6,376,190, entitled "Modified SELEX Processes Without Purified Protein." In the instant case, the target is 4-1BB (CD137).

Aptamers

The aptamers of the instant disclosure were identified using the improved SELEX method for identifying aptamers having slow off-rates as described in Example 1, which describes a representative method for the selection and production of DNA aptamers to 4-1BB. Briefly, with reference to Example 1, an in vitro selection was performed for 4-1BB using modified DNA as described in (Vaught et al., J. Am. Chem. Soc., 132:4141-4151, 2010). An RNA aptamer for 4-1BB(TNFRSF9) has been reported (Kd=4×10$^{-8}$ M), but DNA aptamers for this important human protein have not (J.

O. McNamara II, et al., Clin. Invest. 118:376-386, 2008). As a positive control for the DNA in vitro selection methods described, tumor associated calcium signal transducer 2 (TACSTD2) was also used as a protein target in a parallel experiment. TACSTD2 is known to bind random DNA pools with a Kd<$10^{-7}$ M and appeared to be a good target for selection of DNA aptamers, although it should be noted that no DNA aptamers had been reported for this target. The starting random DNA libraries were prepared using standard automated phosphoramidite synthesis on an ABI 3900 synthesizer to give a base composition ratio of ca. 1:1:1:1 A:C:G:T in the 40N random region. These aptamer selection experiments on the protein targets 4-1BB and TACSTD2 were monitored by C0t curve analysis for convergence of the sequence pools. Protein concentrations for the first cycle of selection were on the order of 1 µM and DNA library concentration 1 nM. Selection for affinity binding was driven by decreasing protein concentration during the course of the selection. Both selection experiments were stopped at 8 cycles based on convergence.

The PCR product of the cycle 8 pool was converted into the ssDNA aptamer pool by primer extension methods using KOD as described above. Analysis of these experiments began by measuring the Kd of the DNA and modified DNA aptamer pools using radiolabeled pools in a filter binding assay. A cutoff of 100 nM was used for the Kd measurement with a measured Kd above this value being considered a failure. In support of the notion that TACSTD2 was a suitable control protein, all of the DNA selections (TTP, 6a, 6b, and 6d) yielded aptamers. Good (Kd—9 nM) to excellent (Kd—0.5 nM) binding affinity was observed for this target protein. As had been observed previously, the DNA library derived from TTP resulted in a failed selection for 4-1BB. Selections performed with DNA libraries derived from 6a and 6d yielded sequence pools with Kd values well below the cutoff limit of 100 nM ($10^{-7}$ M). Perhaps most surprisingly, the DNA aptamer pool derived from 6d had a significantly lower Kd for 4-1BB than that reported for the unmodified RNA aptamer. These data clearly show the advantage of using DNA base modifications at the 5-position of the uridine ring in aptamers.

It could not be ruled out from the pool data that the types of modifications used for the aptamers described herein were simply hydrophobic and that the specific structure of the 5-position modification was less important. Moreover, without sequencing and performing base composition analysis on the clones, it was unclear if the modified dU analogues were even tolerated in the structures or of any importance whatsoever. To test this possibility, a representative "hit" sequence was examined for binding to the target protein 4-1BB.

Briefly, the converged pool after eight rounds of SELEX was cloned and sequenced. Selected DNA was PCR amplified with non-biotinylated SELEX primers to create AGCT DNA, purified using a QIAquick 96 PCR Purification Kit (Cat#28181), and purified inserts were cloned using Stratagene PCR-Script Cloning Kit (Cat#211189) as per manufacturer's protocol. The ligated SELEX pools were sent to a sequencing vender (Cogenics, Houston, Tex.) for transformation, array into 96-well plates, DNA prep and sequencing. Sequences for 29 clones were obtained and analyzed for convergence using custom software that determines sequence counts/copy number and identifies common convergence patterns using a local-alignment algorithm. Sequences with highest representation/copy number in the pool and sequences that were converged to common binding motifs were chosen for downstream screening and were prepared enzymatically using plasmid DNA obtained from Cogenics as template for PCR amplification, and primer extension with modified nucleotides as performed during the selection. (see FIG. 5).

Active sequences 1684-40 (SEQ ID NO: 6) and 1684-44 (SEQ ID NO: 7) were both members a sequence family comprising 52% of the sequenced clones. Sequences in this family were distinguished by containing a conserved two-part consensus pattern (see FIG. 9A). The consensus was comprised of 2 noncontiguous sequence strings (A and B) of lengths 9 and 8, respectively separated by non-conserved linker sequence (L1 or L2) of variable length (see FIG. 9B). FIG. 9A depicts the sequences, including affinity-active clones 1684-40 (SEQ ID NO: 6) and 1684-44 (SEQ ID NO: 7), containing the consensus sequences. There are three conserved TrpdU bases in the consensus, two in part A, and one in part B, which may explain in part why substitutions of TrpdU with other nucleotides eliminated the binding activity to the selected target. Positions X, Y and Z of the consensus in contrast, exhibited more than one base among the aligned family members, indicating there is probably some variability tolerated at these 3 (out of 17) consensus positions. The variability at positions X, Y, and Z was limited to 2 bases per position (G/C, or C/T) in the sequences shown. There is no structural information available for these sequences and no obvious co-variation observed. However, the conserved patterns A and B comprising the consensus were found in different orientations relative to the 5' and 3' ends of the random region in half the sequences of this family, indicating they can be circularly permuted (as depicted in FIG. 9B) and are likely critical for the structure and 4-1BB target-binding properties of these sequences. The consensus sequences are shown in FIG. 10, along with a graphic representation of the nucleotide frequency at each position.

From this information the following two consensus sequences were identified:

```
Consensus sequence A: CCCWCWAGX;
and

Consensus sequence B: YCGGAWGZ;
``` wherein
X=G or C;
Y=G or C;
Z=C or W;
and wherein
W is an independently selected modified nucleotide.

In some embodiments, W is a modified uridine as defined above. In other embodiments, W is a C-5 modified pyrimidine as defined above. Many of these nucleotide modifications are anticipated to be equally effective in promoting high affinity binding to 4-1BB and providing a slow off rate.

In some aspects, W is a C-5 modified pyrimidine independently selected from the group consisting of 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-isobutylcarboxyamide)-2'-deoxyuridine (iBudU), 5-(N-isobutylcarboxyamide)-2'-β-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-β-methyluridine, 5-(N-tryptaminocarboxyamide)-2'-fluorouridine, 5-(N-[1-(3-trimethylamonium)propyl]carboxyamide)-2'-deoxyuridine chloride, 5-(N-naphthylmethylcarboxyamide)-2'-deoxyuridine (NapdU), 5-(N-naphthylmethylcarboxyamide)-2'-O-methyluridine, 5-(N-naphthylmethylcarboxyamide)-2'-fluorouridine and 5-(N-[1-(2,3-dihydroxypropyl)]

carboxyamide)-2'-deoxyuridine). In yet other embodiments, W is 5-(N-tryptaminocarboxyamide)-2'-deoxyuridine (TrpdU).

As illustrated in FIG. 8B, the following two consensus models were constructed:

$$5'-5_f-A-L1-B-3_f-3'$$
$$3'-3_f-A-L2-B-5_f-5'$$

wherein
A is consensus sequence A as defined above;
B is consensus sequence B as defined above;
$5_f$ is a 5'-flanking region;
$3_f$ is a 3'-flanking region;
L1 is a first linker (linker 1);
and L2 is a second linker (linker 2);
wherein 5f, 3f, L1 and L2 each have a sequence length independently selected from n=0 to 100 and are comprised of modified or unmodified nucleotides, spacer sequences, or a combination thereof.

As used herein, a "spacer sequence" refers to any sequence comprised of small molecule(s) covalently bound to either end of a consensus region. A "small molecule" refers to a monomeric or oligomeric, low molecular weight, inorganic or organic compound. Examples of spacer sequences include, but are not limited to, polyethylene glycols, hydrocarbon chains, and other polymers or copolymers that provide a molecular covalent scaffold connecting the consensus regions while preserving 4-1BB binding activity. In certain aspects, the spacer sequence may be covalently attached to the consensus region through standard linkages such as the terminal 3' or 5' hydroxyl, 2' carbon, or base modification such as the C5-position of pyrimidines, or C8 position of purines.

More specifically, in one aspect, with reference to FIGS. 9 and 10, the 4-1BB aptamers of the instant disclosure are selected from:

```
                                           (SEQ ID NO: 14)
5'-5f(n)-CCCWCWAGX-L1(n)-YCGGAWGZ-3f(n)-3'

(SEQ ID NO: 15)
3'-3f(n)-CCCWCWAGX-L2(n)-YCGGAWGZ-5f(n)-5'
``` wherein
X=G or C;
Y=G or C;
Z=C or W;
wherein
W is an independently selected modified nucleotide; and C is an independently selected modified C.;
$3_f, 5_f$, L1 and L2 are independently selected from a nucleotide (N), a modified nucleotide, a spacer, or a combination thereof; and
n=an integer from 0-100.

In some embodiments, W is a 5-modified dU and C is a 5-modified dC.

In another aspect, W is TrpdU, C is 5-methyldC, and the consensus sequences are:

```
                                           (SEQ ID NO: 16)
5'-5f(n)-CCCTCTAGX-L1(n)YCGGATGZ-3f(n)-3'

(SEQ ID NO: 17)
3'-3f(n)-CCCTCTAGX-L2(n)YCGGATGZ-5f(n)-5'
``` wherein T is TrpdU, C is 5-modified methyldC, and all other moieties are as defined above.

In another aspect, the 4-1BB aptamers are selected from

```
5'-CCCTCTAGX-N(0-100)-YCGGATGZ-3'   (SEQ ID NO: 18)

3'-CCCTCTAGX-N(0-100)-YCGGATGZ-5'   (SEQ ID NO: 19)
``` wherein T is TrpdU, C is C-5-modified methyl, N is independently selected from any naturally occurring or modified nucleotide and all other moieties are as defined above.

In yet another aspect, the 4-1BB aptamers are selected from

```
5'-CCCTCTAGX-N(0-40)-YCGGATGZ-3'    (SEQ ID NO: 20)

3'-CCCTCTAGX-N(0-40)-YCGGATGZ-5'    (SEQ ID NO: 21)
``` wherein T is TrpdU, C is C-5-modified methyl, N is independently selected from any naturally occurring or modified nucleotide, and all other moieties are is as defined above.

As used herein, "consensus sequence", when used in reference to a series of related nucleic acids, refers to a nucleotide sequence that reflects the most common choice of base at each position in the sequence where the series of related nucleic acids has been subjected to intensive mathematical and/or sequence analysis.

Cloning and sequencing of the cycle 8 aptamer pool from the 6d selection on the 4-1BB target revealed two distinct families. From a sequencing perspective, this selection resulted in a high degree of convergence, making analysis of the major family descriptive of the outcome of the in vitro selection. DNA clone 1684-40 (SEQ ID NO: 6) was chosen for further study because it was a member of a major sequence family. Clone 1684-40 has the following sequence:

```
                                                (SEQ ID NO: 6)
CCTGCACCCAGTGTCCCCGACGGGGCCCTCTAGCCGTACTC

TGTAATGGCGGATGCTGACGGAGAGGAGGACGG
``` wherein the letters in bold italics indicate the sequence evolved from the random region. The base composition of this sequence was representative of the aptamers in this family at 31% C (modified dC), 21% T (modified dU), 31% G, and 17% A. Note that the sequence was prepared enzymatically by primer extension using KOD XL as described above, which means that only positions labeled italicized T will contain a modification within the DNA sequence.

Figure 7:
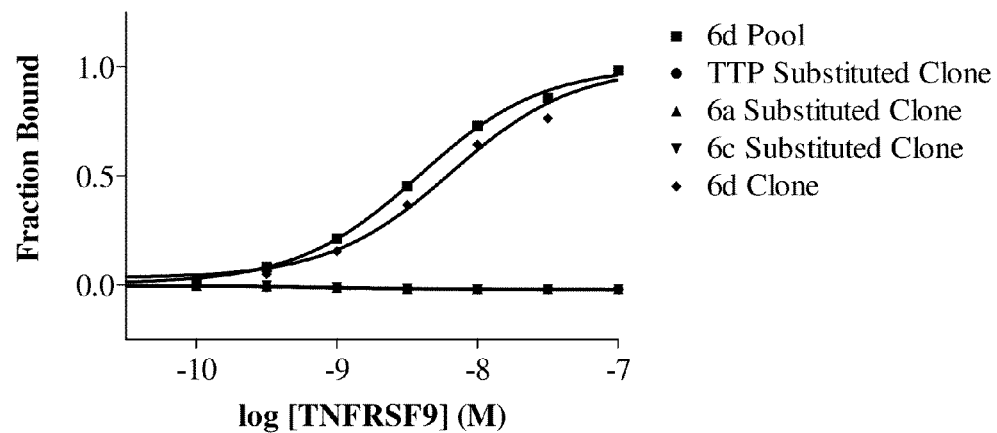
FIG. 7 illustrates graphically the filter binding data for Kd measurements of the in vitro selected DNA sequence clone 1684-40 (SEQ ID NO: 6) and the evolved cycle 8 pool for the protein target TNFRSF9 using TTP, 6a, or 6d for enzymatic preparation. Fraction bound was calculated as the fraction of radiolabeled DNA bound to protein immobilized on beads as a function of protein concentration and normalized to the amount of DNA bound at the curve plateau.

To determine if the binding to 4-1BB was merely a consequence of adding some hydrophobic groups to clone 1684-40 (SEQ ID NO: 6) or a more specific structural effect unique to the C-5 modification used in the selection of this sequence, primer extension reactions were performed using either 6d (C-5 modified tryptamino), 6a (C-5 modified benzyl), or 6c (C-5 modified napthylmethyl) dU analogues. In addition, clone 1684-40 was also transcribed with unmodified TTP to determine if this sequence required modification at all to bind 4-1BB. Employing the same filter binding assay as used to study the evolved DNA aptamer pool binding, and including a control experiment with the cycle 8 aptamer pool, the Kd values were compared and contrasted, as shown in FIG. 7. No Kd was observed within the 100 nM cutoff limits for the DNA aptamer sequence 1684-40 binding 4-1BB when prepared from TTP (red squares). Similarly, clone 1684-40 prepared by enzymatic transcription with either 6a (benzyl) or 6c (naphthylmethyl) gave no binding to 4-1BB within the 100 nM cutoff. In contrast, enzymatic preparation of 1684-40 with 6d (tryptamino) gave a Kd of approximately 5 nM in binding 4-1BB, within experimental error, the same as that observed for the evolved cycle 8 pool.

Clone 1684-40 (SEQ ID NO: 6) was then tested for its ability to block 4-1BB ligand binding to 4-1BB. It was synthesized using standard automated phosphoramidite DNA synthesis along with a dT substituted version where modified dU's were replaced with dT's. Co-immunoprecipitation of 4-1BB ligand by 4-1BB was performed in the presence of either the fully modified aptamer or the dT version, but only the modified aptamer inhibited co-immunoprecipitation demonstrating that this aptamer blocks binding of 4-1BB ligand to its receptor.

The present disclosure provides 4-1BB aptamers identified using the SELEX method and listed in FIG. 8 (SEQ ID NOS: 4-13). Aptamers to 4-1BB that are substantially homologous to any of the listed aptamers and that have a substantially similar ability to bind 4-1BB as that of an aptamer selected from the group of aptamers set forth in FIG. 8 (SEQ ID NOS: 4-13) are also encompassed by the present disclosure. Further, aptamers to 4-1BB that have substantially the same structural form as the aptamers identified herein and that have a substantially similar ability to bind 4-1BB as that of an aptamer selected from the group of aptamers set forth in FIG. 8 (SEQ ID NOS: 4-13) are also encompassed by the present disclosure.

In one aspect, the present disclosure provides an aptamer that specifically binds to 4-1BB and includes a primary nucleic acid sequence. In one embodiment, the primary nucleic acid sequence is selected from SEQ ID NOS: 4-13. In other embodiments, the primary nucleic acid sequence is selected such that it is at least about 75% identical, at least about 80% identical, at least about 85% identical, at least about 90% identical, or at least about 95% identical to a primary nucleic acid sequence selected from SEQ ID NOS: 4-13.

The terms "sequence identity", "percent sequence identity", "percent identity", "% identical", "% identity", and variations thereof, when used in the context of two or more nucleic acid sequences, are used interchangeably to refer to two or more sequences or subsequences that are the same or have a specified percentage of nucleotides that are the same, when compared and aligned for maximum correspondence, as measured using a sequence comparison algorithm or by visual inspection. For sequence comparisons, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith and Waterman, Adv. Appl. Math., 2:482, 1981, by the homology alignment algorithm of Needleman and Wunsch, J. Mol. Biol., 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel, F. M. et al., *Current Protocols in Molecular Biology*, pub. by Greene Publishing Assoc. and Wiley-Interscience (1987)).

One example of an algorithm that is suitable for determining percent sequence identity is the algorithm used in the basic local alignment search tool (hereinafter "BLAST"), see, e.g. Altschul et al., J. Mol. Biol. 215:403-410, 1990 and Altschul et al., Nucleic Acids Res., 15:3389-3402, 1997. Software for performing BLAST analyses is publicly available through the National Center for Biotechnology Information (hereinafter "NCBI"). The default parameters used in determining sequence identity using the software available from NCBI, e.g., BLASTN (for nucleotide sequences) are described in McGinnis et al., Nucleic Acids Res., 32:W20-W25, 2004.

As used herein, when describing the percent identity of a nucleic acid, such as a 4-1BB aptamer, the sequence of which is at least, for example, about 95% identical to a reference nucleotide sequence, it is intended that the nucleic acid sequence is identical to the reference sequence except that the nucleic acid sequence may include up to five point mutations per each 100 nucleotides of the reference nucleic acid sequence. In other words, to obtain a desired nucleic acid sequence, the sequence of which is at least about 95% identical to a reference nucleic acid sequence, up to 5% of the nucleotides in the reference sequence may be deleted or substituted with another nucleotide, or some number of nucleotides up to 5% of the total number of nucleotides in the reference sequence may be inserted into the reference sequence (referred to herein as an insertion). These mutations of the reference sequence to generate the desired sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be any one of the entire nucleotide sequences shown in SEQ ID NOS: 4-13, or any fragment of any of these sequences.

In another aspect, the present disclosure provides a 4-1BB aptamer that, upon binding 4-1BB, modulates a 4-1BB function. In various embodiments, the aptamer modulates a 4-1BB function in vivo. In various embodiments, the 4-1BB aptamer includes a sequence of contiguous nucleotides that are identical to a sequence of contiguous nucleotides included in any of SEQ ID NOS: 4-13. In various embodiments, the sequence of contiguous nucleotides in the 4-1BB aptamer can include any number of nucleotides that are identical to the same number of nucleotides in a sequence of contiguous nucleotides included in any of SEQ ID NOS: 4-13. In various embodiments, the sequence of contiguous nucleotides in the 4-1BB aptamer includes a sequence of from about 4 to about 30 contiguous nucleotides that are identical to a sequence of from about 4 to about 30 contiguous nucleotides included in any of SEQ ID NOS: 4-13. In an exemplary embodiment, the 4-1BB aptamer includes a sequence of 30 contiguous nucleotides that are identical to a sequence of 30 contiguous nucleotides included in any of SEQ ID NOS: 4-13. In another exemplary embodiment, the 4-1BB aptamer includes a sequence of 20 contiguous nucleotides that are identical to a sequence of 20 contiguous nucleotides included in any of SEQ ID NOS: 4-13. In yet another exemplary embodiment, the 4-1BB aptamer includes a sequence of 8 contiguous nucleotides that are identical to a sequence of 8 contiguous nucleotides included in any of SEQ ID NOS: 4-13. In yet another exemplary embodiment, the 4-1BB aptamer includes a sequence of 4 contiguous nucleotides that are identical to a sequence of 4 contiguous nucleotides included in any of SEQ ID NOS: 4-13.

In one embodiment, the 4-1BB aptamer is SEQ ID NOS: 4-13. In another embodiment, the 4-1BB aptamer is SEQ ID NOS: 4-13. In yet another embodiment, the β-4-1BB aptamer is derived from the consensus sequence of SEQ ID NOS: 4-13. In other embodiments, the 4-1BB aptamer is any of SEQ ID NOS: 4-13. In one embodiment, the 4-1BB aptamer is at least about 95% identical, at least about 90% identical, at least about 85% identical, at least about 80% identical, or at least about 75% identical to any of SEQ ID NOS: 4-13. In another embodiment, the 4-1BB aptamer includes a sequence from any of SEQ ID NOS: 4-13 and fragments of any of these.

The 4-1BB aptamer can contain any number of nucleotides in addition to the 4-1BB binding region. In various embodiments, the 4-1BB aptamer can include up to about 100 nucleotides, up to about 95 nucleotides, up to about 90 nucleotides, up to about 85 nucleotides, up to about 80 nucleotides, up to about 75 nucleotides, up to about 70 nucleotides, up to about 65 nucleotides, up to about 60 nucleotides, up to about 55 nucleotides, up to about 50 nucleotides, up to about 45 nucleotides, up to about 40 nucleotides, up to about 35 nucleotides, up to about 30 nucleotides, up to about 25 nucleotides, and up to about 20 nucleotides.

The 4-1BB aptamer can be selected to have any suitable dissociation constant ($K_d$) for 4-1BB. In an exemplary embodiment, the 4-1BB aptamer has a dissociation constant ($K_d$) for 4-1BB of about 10 nM or less. In another exemplary embodiment, the 4-1BB aptamer has a dissociation constant ($K_d$) for 4-1BB of about 15 nM or less. In yet another exemplary embodiment, the 4-1BB aptamer has a dissociation constant ($K_d$) for 4-1BB of about 20 nM or less. In yet another exemplary embodiment, the 4-1BB aptamer has a dissociation constant ($K_d$) for 4-1BB of about 25 nM or less. In yet another exemplary embodiment, the 4-1BB aptamer has a dissociation constant ($K_d$) for 4-1BB of about 30 nM or less. In yet another exemplary embodiment, the 4-1BB aptamer has a dissociation constant ($K_d$) for 4-1BB of about 35 nM or less. In yet another exemplary embodiment, the 4-1BB aptamer has a dissociation constant ($K_d$) for 4-1BB of about 40 nM or less. In yet another exemplary embodiment, the 4-1BB aptamer has a dissociation constant ($K_d$) for 4-1BB of about 45 nM or less. In yet another exemplary embodiment, the 4-1BB aptamer has a dissociation constant ($K_d$) for 4-1BB of about 50 nM or less. In yet another exemplary embodiment, the 4-1BB aptamer has a dissociation constant ($K_d$) for 4-1BB in a range of about 3-10 nM. A suitable dissociation constant can be determined with a binding assay using a multi-point titration and fitting the equation $y=(max-min)(Protein)/(K_d+Protein)+min$ as described in Example 1, below. It is to be understood that the determination of dissociation constants is highly dependent upon the conditions under which they are measured and thus these numbers may vary significantly with respect to factors such as equilibration time, etc. In other embodiments, the 4-1BB aptamer is an aptamer with a $K_d$ that is less than or equal to the $K_d$ of an aptamer selected from SEQ ID NOS: 4-13.

Pharmaceutical Compositions Including a 4-1BB Aptamer

The present disclosure encompasses pharmaceutical compositions that include at least one aptamer to 4-1BB and at least one pharmaceutically acceptable carrier. Suitable carriers are described in "Remington: The Science and Practice of Pharmacy, Twenty-first Edition," published by Lippincott Williams & Wilkins, which is incorporated herein by reference. Pharmaceutical compositions that include at least one aptamer to 4-1BB and at least one pharmaceutically acceptable carrier may also include one or more active agents that are not a 4-1BB aptamer.

The aptamers described herein can be utilized in any pharmaceutically acceptable dosage form, including but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc. Specifically, the aptamers described herein can be formulated: (a) for administration selected from any of oral, pulmonary, intravenous, intra-arterial, intrathecal, intra-articular, rectal, ophthalmic, colonic, parenteral, intracisternal, intravaginal, intraperitoneal, local, buccal, nasal, and topical administration; (b) into a dosage form selected from any of liquid dispersions, gels, aerosols, ointments, creams, tablets, sachets and capsules; (c) into a dosage form selected from any of lyophilized formulations, dry powders, fast melt formulations, controlled release formulations, delayed release formulations, extended release formulations, pulsatile release formulations, and mixed immediate release and controlled release formulations; or (d) any combination thereof.

Solutions or suspensions used for parenteral, intradermal, or subcutaneous application can comprise one or more of the following components: (1) a sterile diluent such as water for injection, saline solution, fixed oils, polyethylene glycols, glycerine, propylene glycol or other synthetic solvents; (2) antibacterial agents such as benzyl alcohol or methyl parabens; (3) antioxidants such as ascorbic acid or sodium bisulfite; (4) chelating agents such as ethylenediaminetetraacetic acid; (5) buffers such as acetates, citrates or phosphates; and (5) agents for the adjustment of tonicity such as sodium chloride or dextrose. The pH can be adjusted with acids or bases, such as hydrochloric acid or sodium hydroxide. A parenteral preparation can be enclosed in ampoules, disposable syringes or multiple dose vials made of glass or plastic.

Pharmaceutical compositions suitable for injectable use may include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition should be sterile and should be fluid to the extent that easy syringability exists. The pharmaceutical composition should be stable under the conditions of manufacture and storage and should be preserved against the contaminating action of microorganisms such as bacteria and fungi. The term "stable", as used herein, means remaining in a state or condition that is suitable for administration to a patient.

The carrier can be a solvent or dispersion medium, including, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol or sorbitol, and inorganic salts such as sodium chloride in the composition. Prolonged absorption of the injectable compositions can be brought about by including in the composition an agent which delays absorption, for example, aluminum monostearate and gelatin.

Sterile injectable solutions can be prepared by incorporating the active reagent (e.g., a 4-1BB aptamer) in the required amount in an appropriate solvent with one or a combination of ingredients enumerated above, as required, followed by filtered sterilization. Generally, dispersions are prepared by incorporating at least one 4-1BB aptamer into a sterile vehicle that contains a basic dispersion medium and any other required ingredient. In the case of sterile powders for the preparation of sterile injectable solutions, exemplary methods of preparation include vacuum drying and freeze-drying, both of which will yield a powder of the 4-1BB aptamer plus any additional desired ingredient from a previously sterile-filtered solution thereof.

Oral compositions generally include an inert diluent or an edible carrier. They can be enclosed, for example, in gelatin capsules or compressed into tablets. For the purpose of oral therapeutic administration, the 4-1BB aptamer can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For administration by inhalation, the compounds are delivered in the form of an aerosol spray from a pressured container or dispenser that contains a suitable propellant, e.g., a gas such as carbon dioxide, a nebulized liquid, or a dry powder from a suitable device. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams as generally known in the art. The reagents can also be prepared in the form of suppositories (e.g., with conventional suppository bases such as cocoa butter and other glycerides) or retention enemas for rectal delivery.

In one embodiment, a 4-1BB aptamer is prepared with a carrier that will protect against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, suspensions of the 4-1BB aptamer may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also include suitable stabilizers or agents to increase the solubility of the compounds and allow for the preparation of highly concentrated solutions.

In some cases, it may be especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of a 4-1BB aptamer calculated to produce the desired therapeutic effect in association with the required pharmaceutical carrier. The specification for the dosage unit forms of the 4-1BB aptamers described herein are dictated by and directly dependent on the unique characteristics of the particular 4-1BB aptamer and the particular therapeutic effect to be achieved, and the limitations inherent in the art of compounding such an active agent for the treatment of individuals.

Pharmaceutical compositions comprising at least one 4-1BB aptamer can include one or more pharmaceutical excipients. Examples of such excipients include, but are not limited to, binding agents, filling agents, lubricating agents, suspending agents, sweeteners, flavoring agents, preservatives, buffers, wetting agents, disintegrants, effervescent agents, and other excipients. Such excipients are known in the art. Exemplary excipients include: (1) binding agents which include various celluloses and cross-linked polyvinylpyrrolidone, microcrystalline cellulose, such as Avicel® PH101 and Avicel® PH102, silicified microcrystalline cellulose (Pro-Solv SMCC™), gum tragacanth and gelatin; (2) filling agents such as various starches, lactose, lactose monohydrate, and lactose anhydrous; (3) disintegrating agents such as alginic acid, Primogel, corn starch, lightly crosslinked polyvinyl pyrrolidone, potato starch, maize starch, and modified starches, croscarmellose sodium, cross-povidone, sodium starch glycolate, and mixtures thereof; (4) lubricants, including agents that act on the flowability of a powder to be compressed, include magnesium stearate, colloidal silicon dioxide, such as Aerosil® 200, talc, stearic acid, calcium stearate, and silica gel; (5) glidants such as colloidal silicon dioxide; (6) preservatives, such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride; (7) diluents such as pharmaceutically acceptable inert fillers, such as microcrystalline cellulose, lactose, dibasic calcium phosphate, saccharides, and/or mixtures of any of the foregoing; examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose; (8) sweetening agents, including any natural or artificial sweetener, such as sucrose, saccharin sucrose, xylitol, sodium saccharin, cyclamate, aspartame, and acesulfame; (9) flavoring agents, such as peppermint, methyl salicylate, orange flavoring, Magnasweet® (trademark of MAFCO), bubble gum flavor, fruit flavors, and the like; and (10) effervescent agents, including effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

In various embodiments, the formulations described herein are substantially pure. As used herein, "substantially pure" means the active ingredient (4-1BB aptamer) is the predominant species present (i.e., on a molar basis it is more abundant than any other individual species in the composition). In one embodiment, a substantially purified fraction is a composition wherein the active ingredient comprises at least about 50 percent (on a molar basis) of all macromolecular species present. Generally, a substantially pure composition will include more than about 80% of all macromolecular species present in the composition. In various embodiments, a substantially pure composition will include at least about 85%, at least about 90%, at least about 95%, or at least about 99% of all macromolecular species present in the composition. In various embodiments, the active ingredient is purified to essential homogeneity (contaminant species cannot be detected in the composition by conventional detection methods) wherein the composition consists essentially of a single macromolecular species.

Kits Comprising 4-1BB Aptamer Compositions

The present disclosure provides kits comprising any of the 4-1BB aptamers described herein. Such kits can comprise, for example, (1) at least one 4-1BB aptamer; and (2) at least one pharmaceutically acceptable carrier, such as a solvent or solution. Additional kit components can optionally include, for example: (1) any of the pharmaceutically acceptable excipients identified herein, such as stabilizers, buffers, etc., (2) at least one container, vial or similar apparatus for holding and/or mixing the kit components; and (3) delivery apparatus.

Methods of Treatment

The present disclosure provides methods of preventing or treating (e.g., alleviating one or more symptoms of) medical conditions through the use of a 4-1BB aptamer. The methods comprise administering a therapeutically effective amount of a 4-1BB aptamer to a patient in need thereof. The described aptamers can also be used for prophylactic therapy.

The 4-1BB aptamer used in methods of treatment can be: (1) a novel 4-1BB aptamer prepared by the methods described herein, or a pharmaceutically acceptable salt thereof, or a prodrug thereof.

The individual or patient can be any animal (domestic, livestock or wild), including, but not limited to, cats, dogs, horses, pigs and cattle, and preferably human patients. As used herein, the terms patient, individual, and subject may be used interchangeably.

As used herein, "treating" describes the management and care of a patient for the purpose of treating a disease, condition, or disorder and includes the administration of a 4-1BB aptamer to prevent the onset of the symptoms or complications of a disease, condition or disorder; to alleviate symptoms or complications of the disease, condition, or disorder; or to eliminate the presence of the disease, condition or disorder in the patient. More specifically, "treating" includes reversing, attenuating, alleviating, minimizing, suppressing or halting at least one deleterious symptom or effect of a disease (disorder) state, disease progression, disease causative agent (e.g., bacteria or viruses), or other abnormal condition. Treatment is generally continued as long as symptoms and/or pathology ameliorate.

"Combination therapy" (or "co-therapy") includes the administration of a 4-1BB aptamer composition and at least one second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" may, but generally is not, intended to encompass the administration of two or more of these therapeutic agents as part of separate monotherapy regimens that incidentally and arbitrarily result in the combinations of the present disclosure. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dose having a fixed ratio of each therapeutic agent or in multiple, single doses for each of the therapeutic agents.

The dosage regimen utilizing the 4-1BB aptamers is selected in accordance with a variety of factors, including, for example, type, species, age, weight, sex and medical condition of the patient; the severity of the condition to be treated; the route of administration; the renal and hepatic function of the patient; and the particular 4-1BB aptamer or salt thereof employed. An ordinarily skilled physician or veterinarian can readily determine and prescribe the effective amount of the composition required to prevent, counter or arrest the progress of the condition.

In general, the dosage, i.e., the therapeutically effective amount, ranges from about 1 µg to about 100 mg/kg body weight of the subject being treated, per day.

EXAMPLES

The following examples are provided for illustrative purposes only and are not intended to limit the scope of the invention as defined by the appended claims. All examples described herein were carried out using standard techniques, which are well known and routine to those of skill in the art. Routine molecular biology techniques described in the following examples can be carried out as described in standard laboratory manuals, such as Sambrook et al., Molecular Cloning: A Laboratory Manual, 3rd. ed., Cold Spring Harbor Laboratory Press, Cold Spring Harbor, N.Y., (2001).

Example 1

Aptamer Selection and Sequences

In Vitro Selection

Figure 5:
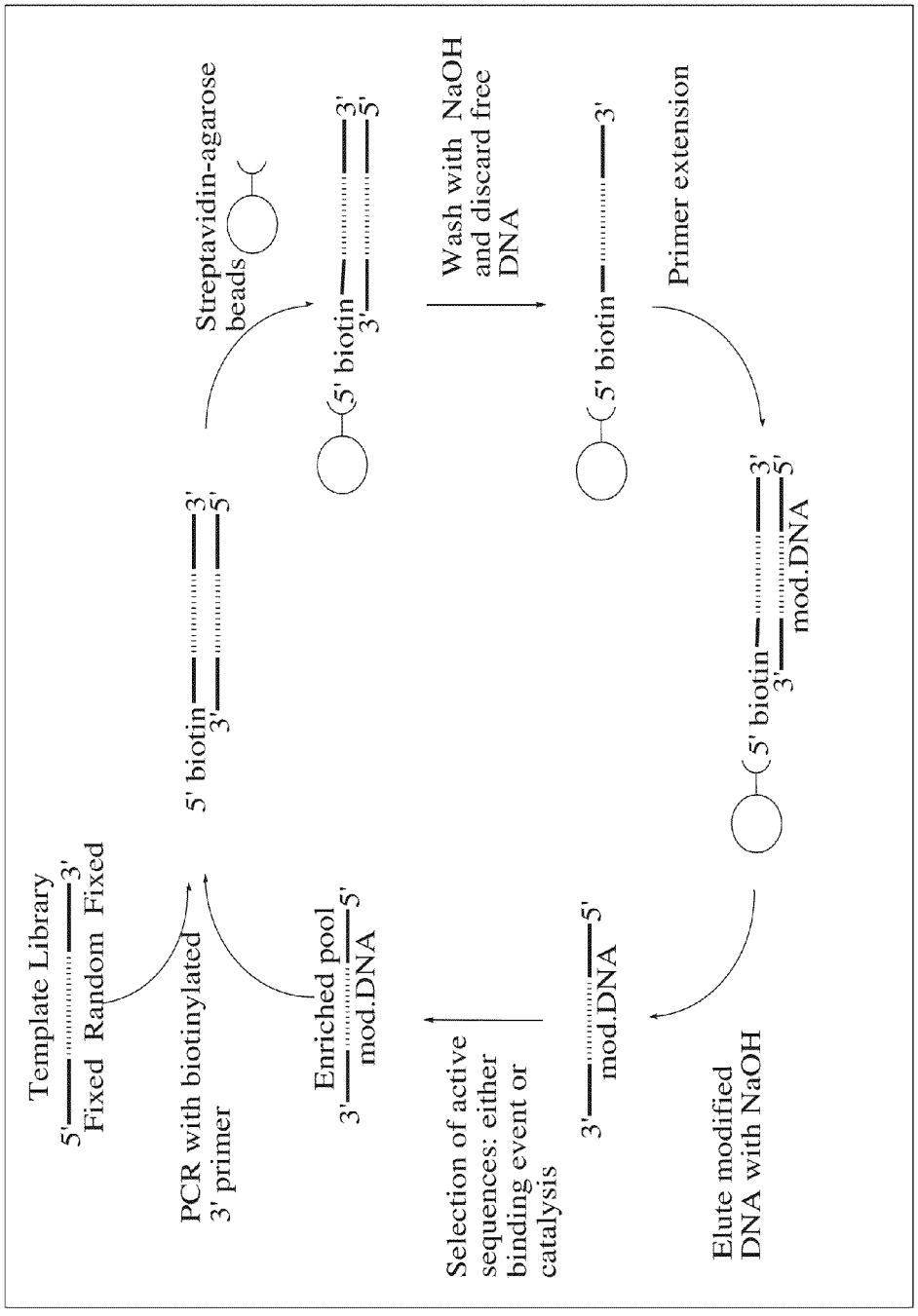
FIG. 5 illustrates an exemplary modified DNA SELEX selection scheme.
Figure 6:
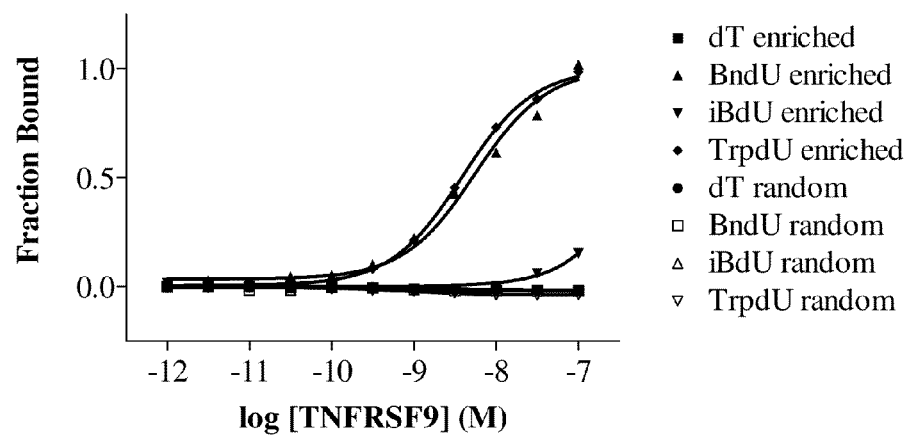
FIG. 6 illustrates graphically the filter binding data for Kd measurements of the in vitro selected pools and the starting random libraries using TTP, 6a, 6b, or 6d for TNFRSF9. Note that for TTP "selected" and TTP random, no binding was observed in either case. Fraction bound was calculated as the fraction of radiolabeled DNA bound to protein immobilized on beads as a function of protein concentration and normalized to the amount of DNA bound at the curve plateau.

The in vitro selection scheme used herein is illustrated schematically in FIG. 5. Specifically, DNA and modified DNA libraries were prepared with dATP, dGTP, 5-methyl-dCTP (MedCTP), and either dTTP or one of three dUTP analogues: 6a, 6b, or 6d. Candidate mixtures were prepared by polymerase extension of a primer annealed to a biotinylated template (5'-ABABCCGTCCTCCTCTCCGT-40N-GGGACACTGGGTGCAGG-3') (SEQ ID NO: 1), where B indicates a biotin incorporated during DNA synthesis and 40N indicates a 40 nucleotide random region. For each candidate mixture composition, 4.8 nmol forward PCR primer (5'-ATATATATCCTGCACCCAGTGTCCC-3') (SEQ ID NO: 2) and 4 nmol template were combined in 100 µL 1×KOD DNA polymerase buffer (Novagen), heated to 95° C. for 8 min, and cooled on ice. Each 100 µL primer/template mixture was added to a 400 µL extension reaction containing 1×KOD DNA polymerase buffer, 0.125 U/µL KOD DNA polymerase (Novagen), and 0.5 mM each dATP, MedCTP, dGTP, and dTTP or dUTP analogue and incubated at 70° C. for 30 min. Double-stranded product was captured via the template strand biotins by adding 1 mL of streptavidin-coated magnetic beads (Magna-Bind Streptavidin, Pierce, 5 mg/mL in 1 M NaCl+0.05% Tween-20) and incubating at 25° C. for 10 min with mixing. Beads were washed three times with 0.75 mL of SB1T buffer (40 mM HEPES, pH 7.5, 125 mM NaCl, 5 mM KCl, 1 mM $MgCl_2$, 1 mM $CaCl_2$, 0.05% Tween-20). The aptamer strand was eluted from the beads with 1.2 mL of 20 mM NaOH, neutralized with 0.3 mL of 80 mM HCl, and buffered with 15 µL of 1 M HEPES, pH 7.5. Candidate mixtures were concentrated with a Centricon-30 to approximately 0.2 mL and quantified by UV absorbance spectroscopy.

The extracellular domains of 4-1BB (TNFRSF9) and TAC-STD2 fused to IgG1 and 6-His were purchased from R&D Systems. 4-1BB and TACSTD2 were immobilized on $Co^{2+}$-NTA paramagnetic beads (TALON, Dynal). Target proteins were diluted to 0.2 mg/mL in 0.5 mL of B/W buffer (50 mM Na-phosphate, pH 8.0, 300 mM NaCl, 0.01% Tween-20) and added to 0.5 mL of TALON beads (prewashed three times with B/W buffer and resuspended to 10 mg/mL in B/W buffer). The mixture was rotated for 30 min at 25° C. and stored at 4° C. until use. TALON beads coated with $(His)_6$ peptide were also prepared and stored as above. Prior to use, beads were washed three times with B/W buffer, once with SB1T, and resuspended in SB1T.

Affinity selections were performed separately with each candidate mixture, comparing binding between target protein beads (signal) and (His)6 beads (background). For each sample, a 0.5 µM candidate DNA mixture was prepared in 40 µL of SB1T. Ten microliters of a protein competitor mixture was added to each DNA mix (0.1% HSA, 10 µM casein, and 10 µM prothrombin in SB1T).

Binding reactions were performed by adding 50 µL target protein coated beads or (His)6-coated beads (5 mg/mL in SB1T) to the DNA mixture and incubating at 37° C. for 15 min with mixing. The DNA solution was removed, and the beads were washed five times at 37° C. with SB1T containing 0.1 mg/mL herring sperm DNA (Sigma-Aldrich). Unless indicated, all washes were performed by resuspending the beads in 100 µL wash solution, mixing for 30 s, separating the beads with a magnet, and removing the wash solution. Bound aptamers were eluted from the beads by adding 100 µL of SB1T+2 M guanidine-HCl and incubating at 37° C. for 5 min with mixing. The aptamer eluate was transferred to a new tube after magnetic separation. After the first two selection rounds, the final two of five target bead washes were done for 5 min instead of 30 s.

Primer beads were prepared by immobilizing biotinylated reverse PCR primer (5'-ABABTTTTTTTTCCGTCCTC-CTCTCCGTC-3') (SEQ ID NO: 3) to streptavidin-coated paramagnetic beads (MyOne-SA, Dynal). Five milliliter MyOne-SA beads (10 mg/mL) were washed once with NaClT (5 M NaCl, 0.01% Tween-20) and resuspended in 5 mL of biotinylated reverse PCR primer (5 µM in NaClT). The sample was incubated at 25° C. for 15 min, washed twice with 5 mL of NaClT, resuspended in 12.5 mL of NaClT (4 mg/mL), and stored at 4° C.

Twenty-five microliter primer beads (4 mg/mL in NaClT) were added to the 100 µL aptamer solution in guanidine buffer and incubated at 50° C. for 15 min with mixing. The aptamer solution was removed, and the beads were washed five times with SB1T. Aptamer was eluted from the beads by adding 85 µL of 20 mM NaOH and incubating at 37° C. for 1 min with mixing. Eighty microliters of aptamer eluate was transferred to a new tube after magnetic separation, neutralized with 20 µL of 80 mM HCl, and buffered with 1 µL of 0.5 M Tris-HCl, pH 7.5.

Selected aptamer DNA was amplified and quantified by QPCR. Forty-eight microliters of DNA was added to 12 µL of QPCR Mix (5×KOD DNA polymerase buffer, 25 mM $MgCl_2$, 10 µM forward PCR primer, 10 µM biotinylated reverse PCR primer, 5×SYBR Green I, 0.125 U/µL KOD DNA polymerase, and 1 mM each dATP, dCTP, dGTP, and dTTP) and thermal cycled in an ABI5700 QPCR instrument with the following protocol: 1 cycle of 99.9° C., 15 s, 55° C., 10 s, 70° C., 30 min; 30 cycles of 99.9° C., 15 s, 72° C., 1 min. Quantification was done with the instrument software, and the number of copies of DNA selected with target beads and (His)6 beads was compared to determine signal/background ratios.

Following amplification, the PCR product was captured on MyOne-SA beads via the biotinylated antisense strand; 1.25 mL MyOne-SA beads (10 mg/mL) were washed twice with 0.5 mL of 20 mM NaOH, once with 0.5 mL of SB1T, resuspended in 2.5 mL of 3 M NaCl, and stored at 4° C. Twenty-five microliter MyOne-SA beads (4 mg/mL in 3 M NaCl) were added to 50 µL double-stranded QPCR product and incubated at 25° C. for 5 min with mixing. The beads were washed once with SB1T, and the "sense" strand was eluted from the beads by adding 200 µL of 20 mM NaOH and incubating at 37° C. for 1 min with mixing. The eluted strand was discarded, and the beads were washed three times with SB1T and once with 16 mM NaCl. Aptamer sense strand was then prepared with the appropriate nucleotide composition as described above and the whole cycle repeated.

Kd Measurements

Affinities of the enriched libraries were measured using TALON bead partitioning. DNA was renatured by heating to 95° C. and slowly cooling to 37° C. Complexes were formed by mixing a low concentration of radiolabeled DNA ($\sim 1\times10^{-11}$ M) with a range of concentrations of target protein ($1\times10^{-7}$ to $1\times10^{-12}$ M final) in SB1 buffer and incubating at 37° C. A portion of each reaction was transferred to a nylon membrane and dried to determine total counts in each reaction. Twenty-five micrograms of MyOne TALON beads (Invitrogen) was added to the remainder of each reaction and mixed at 37° C. for 1 min. A portion was then passed through a MultiScreen HV plate under vacuum to separate protein-bound complexes from unbound DNA and washed with 100 µL of SB1 buffer. The nylon membranes and MultiScreen HV plates were phosphorimaged, and the amount of radioactivity in each sample was quantified using a FUJI FLA-3000. The fraction of captured DNA was plotted as a function of protein concentration, and a nonlinear curve-fitting algorithm was used to extract equilibrium binding constants (Kd values) from the data.

4-1BB Co-Immunoprecipitation

10 µg of Protein A conjugated magnetic beads (Invitrogen) were washed three times with PBS/0.02% Tween-20, and suspended in 100 µL PBS/0.02% Tween-20 with 0.5 µg recombinant human 4-1BB Receptor/Fc Chimera (R&D Systems). The receptor was captured by mixing at room temperature for 15 minutes, put on a magnet, and the supernatant was removed. The beads were washed twice for 1 minute each with 100 µL PBS/0.02% Tween-20 to remove un-bound 4-1BB receptor, and 100 μL of heat/cooled (95° C. 3 minutes, slow cool to 37° C. at 0.1° C./second) SOMAmer in PBS/ 0.02% Tween-20 at various concentrations was added to the beads, and allowed to equilibrate for 1 hour at 37° C. with shaking. 0.25 μg of recombinant 4-1BB Ligand (R&D Systems) was added to each reaction and allowed to bind for 15 minutes at 37° C. with shaking. The beads were then washed three times for 1 minute each with 100 μL PBS/0.02% Tween-20 to remove un-bound 4-1BB ligand and SOMAmer, and the beads were heated in 14 μL 1×LDS Sample Buffer (Invitrogen) at 70° C. for 10 minutes, and 5 μL of the reaction was loaded and run on a 4-12% Bis-Tris SDS-PAGE gel in MOPS running buffer (Invitrogen) and stained with SYPRO-Ruby protein stain per manufacturer's instructions (Invitrogen). The bands were quantified by densitometry using Alpha Innotech Imaging software, normalized to a no-ligand control (100%) and a no-SOMAmer control (0%), and plotted vs. the concentration of SOMAmer.

The foregoing embodiments and examples are intended only as examples. No particular embodiment, example, or element of a particular embodiment or example is to be construed as a critical, required, or essential element or feature of any of the claims. Further, no element described herein is required for the practice of the appended claims unless expressly described as "essential" or "critical." Various alterations, modifications, substitutions, and other variations can be made to the disclosed embodiments without departing from the scope of the present invention, which is defined by the appended claims. The specification, including the figures and examples, is to be regarded in an illustrative manner, rather than a restrictive one, and all such modifications and substitutions are intended to be included within the scope of the invention. Accordingly, the scope of the invention should be determined by the appended claims and their legal equivalents, rather than by the examples given above. For example, steps recited in any of the method or process claims may be executed in any feasible order and are not limited to an order presented in any of the embodiments, the examples, or the claims.

What is claimed is:

1. An aptamer comprising the sequence of SEQ ID NO: 14:

$$5'-CCCWCWAGX-L1_{(n)}-YCGGAWGZ-3'$$

wherein,
X is a G or a C;
Y is a G or a C;
Z is a C or a W;

wherein,
each W is independently a modified pyrimidine; and
each C is independently a modified cytidine;

wherein
L1 is independently selected from a nucleotide, a spacer sequence, or a combination thereof; and
n is an integer from 0 to 14.

2. The aptamer of claim 1, wherein said modified pyrimidine is a C-5 modified pyrimidine and said modified cytidine is a C-5 modified cytidine.

3. The aptamer of claim 2, wherein said C-5 modified pyrimidine is selected from the group consisting of the C-5 modified pyrimidines of FIG. 3.

4. The aptamer of claim 2, wherein said C-5 modified pyrimidine is selected from the group consisting of 5-(N-benzylcarboxyamide)-2'-deoxyuridine (BndU), 5-(N-isobutylcarboxyamide)-2'-deoxyuridine (iBudU), 5-(N-tryptaminocarboxyamide)-2'-deoxyuridine (TrpdU) and 5-(N-naphthylmethylcarboxyamide)-2'-deoxyuridine (NapdU).

5. The aptamer of claim 2, wherein said C-5 modified pyrimidine is 5-(N-tryptaminocarboxyamide)-2'-deoxyuridine (TrpdU).

6. The aptamer of claim 2, wherein said C-5 modified cytidine is 5-methylcytidine.

7. The aptamer of claim 1, wherein the aptamer binds to a 4-1BB protein.

8. The aptamer of claim 7, wherein the Kd of said aptamer-4-1BB protein interaction is 50 nM or less.

9. The aptamer of claim 7, wherein said aptamer has the ability to inhibit the binding of a 4-1BB protein to a 4-1BB receptor ligand (4-1BBL).

10. An aptamer that binds to a 4-1BB protein, the aptamer comprising a sequence having at least about 90% identity to a sequence selected from the group consisting of SEQ ID NOS: 4-13.

11. The aptamer of claim 10, wherein said aptamer has the ability to inhibit the binding of a 4-1BB to a 4-1BB receptor ligand (4-1BBL).

12. The aptamer of claim 10, wherein the sequence has at least about 91%, 92%, 93%, 94% or 95% identity to a sequence selected from the group consisting of SEQ ID NOS: 4-13.

13. A pharmaceutical composition comprising an aptamer having a sequence having at least about 90% identity to a sequence selected from the group consisting of SEQ ID NOS: 4-13, or a pharmaceutically acceptable salt thereof.

14. The pharmaceutical composition of claim 13, wherein the sequence has at least about 91%, 92%, 93%, 94% or 95% identity to a sequence selected from the group consisting of SEQ ID NOS: 4-13.

15. A pharmaceutical composition comprising an aptamer having the sequence of CCTGCACCCAGTGTCCCCGACGGGGCCCTCTAGCCGTACTCTGTAATGGCGGATGCTGACGGAGAGGAGGACGG (SEQ ID NO:6); or a pharmaceutically acceptable salt thereof.

* * * * *